US012571044B2

(12) United States Patent
Khatri et al.

(10) Patent No.: US 12,571,044 B2
(45) Date of Patent: Mar. 10, 2026

(54) CLASSIFIER FOR IDENTIFICATION OF ROBUST SEPSIS SUBTYPES

(71) Applicant: The Board of Trustees of the Leland Stanford Junior University, Stanford, CA (US)

(72) Inventors: Purvesh Khatri, Menlo Park, CA (US); Timothy E. Sweeney, San Francisco, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 1053 days.

(21) Appl. No.: 16/969,923

(22) PCT Filed: Jan. 28, 2019

(86) PCT No.: PCT/US2019/015462
§ 371 (c)(1),
(2) Date: Aug. 13, 2020

(87) PCT Pub. No.: WO2019/168622
PCT Pub. Date: Sep. 6, 2019

(65) Prior Publication Data
US 2022/0220556 A1     Jul. 14, 2022

Related U.S. Application Data

(60) Provisional application No. 62/636,096, filed on Feb. 27, 2018.

(51) Int. Cl.
| | |
|---|---|
| *C12Q 1/68* | (2018.01) |
| *C12P 19/34* | (2006.01) |
| *C12Q 1/6883* | (2018.01) |
| *G16B 25/10* | (2019.01) |
| *G16B 40/20* | (2019.01) |
| *G16B 40/30* | (2019.01) |

(52) U.S. Cl.
CPC ........... *C12Q 1/6883* (2013.01); *G16B 25/10* (2019.02); *C12Q 2600/112* (2013.01); *C12Q 2600/158* (2013.01); *C12Q 2600/16* (2013.01); *G16B 40/20* (2019.02); *G16B 40/30* (2019.02)

(58) Field of Classification Search
CPC ........ C12Q 2600/158; C12Q 2600/112; C12Q 1/6883
See application file for complete search history.

(56) References Cited

U.S. PATENT DOCUMENTS

| | | | |
|---|---|---|---|
| 2009/0010908 A1* | 1/2009 | Gow .................... | C12Q 1/6883 506/13 |
| 2015/0037320 A1 | 2/2015 | McGrath et al. | |
| 2017/0022568 A1 | 1/2017 | Ghazal et al. | |

| | | | |
|---|---|---|---|
| 2017/0058348 A1 | 3/2017 | Stuhlmüller et al. | |
| 2019/0144943 A1 | 5/2019 | Khatri et al. | |
| 2019/0300959 A1 | 10/2019 | Khatri et al. | |
| 2020/0131577 A1 | 4/2020 | Khatri et al. | |

FOREIGN PATENT DOCUMENTS

| | | |
|---|---|---|
| CN | 105518153 A | 4/2016 |
| WO | WO2015121417 A1 | 8/2015 |
| WO | WO2015135071 A1 | 9/2015 |
| WO | WO 2018/004806 A1 | 1/2018 |

OTHER PUBLICATIONS

Hector R. Wong, et al. "Genome-level expression profiles in pediatric septic shock indicate a role for altered zinc homeostasis in poor outcome" Physiol Genomics30: 146-155, 2007. (Year: 2007).*
Ephraim L Tsalik, et al. "An integrated transcriptome and expressed variant analysis of sepsis survival and death" Genome Med. Nov. 2, 20146;6(11):111. (Year: 2014).*
Vivian G. Cheung, et al."Natural variation in human gene expression assessed in lymphoblastoid cells" Nature Genetics, vol. 33, (Mar. 2003) (Year: 2003).*
J. Perren Cobb, et al "Sepsis gene expression profiling: Murine splenic compared with hepatic responses determined by using complementary DNA microarrays" Crit Care Med 2002 vol. 30, No. 12. (Year: 2002).*
Y. Hoshikawa, et al. "Hypoxia induces different genes in the lungs of rats compared with mice" Physiol Genomics 12: 209-219, 2003. (Year: 2003).*
Various authors, Meeting Abstracts, Sepsis 2017 Paris, Intensive Care Medicine Experimental, 2017, 5(Suppl 1):37, pp. 1-40.
Sweeney et al., "A community approach to mortality prediction in sepsis via gene expression analysis", Nature Communications, 2018; 9 (1): 694.
Burnham et al., "Shared and Distinct Aspects of the Sepsis Transcriptomic Response to Fecal Peritonitis and Pneumonia", Am J Respir Crit Care Med, 2017 196(3): 328-339.
Davenport et al., "Genomic landscape of the individual host response and outcomes in sepsis: a prospective cohort study", Lancet Respir Med, 2016, 4: 259-271.
Mncent, "Individual gene expression and personalised medicine in sepsis", The Lancet, 2016, 4: 242-243.
Wong et al., "Identification of pediatric septic shock subclasses based on genome-wide expression profiling", BMC Medicine, 2009, 7: 34.
Wong et al., "Validation of a gene expression-based subclassification strategy for pediatric septic shock", Crit Care Med, 2011, 39(11): 2511-2517.
Wong et al., "Developing a clinically feasible personalized medicine approach to pediatric septic shock", Am J Respir Crit Care Med, 2015, 191(3): 309-315.

* cited by examiner

*Primary Examiner* — Stephen T Kapushoc
(74) *Attorney, Agent, or Firm* — James S. Keddie; Bozicevic, Field & Francis LLP

(57) ABSTRACT

This disclosure provides a gene expression-based method for determining whether a subject having sepsis has an Inflammopathic phenotype, an Adaptive phenotype or a Coagulopathic phenotype. A kit for performing the method is also provided.

9 Claims, 10 Drawing Sheets

CLASSIFIER FOR IDENTIFICATION OF ROBUST SEPSIS SUBTYPES

CROSS-REFERENCING

This application is a § 371 national phase of International Application No. PCT/US2019/015462, filed on Jan. 28, 2019, which claims the benefit of U.S. provisional application Ser. No. 62/636,096, filed on Feb. 27, 2018, which applications are incorporated herein in their entirety.

GOVERNMENT RIGHTS

This invention was made with Government support under contracts AI057229 and AI109662 awarded by the National Institutes of Health. The Government has certain rights in the invention.

BACKGROUND

Sepsis is defined as life-threatening organ dysfunction resulting from a dysregulated immune response to infection (1). Despite its association with nearly half of all in-hospital deaths, there are still no approved therapies specific for sepsis (2, 3). In part, this is because the clinical syndrome of sepsis includes substantial heterogeneity and may in fact encompass many different subtypes, analogous to what is well established among patients with cancer (4, 5). Current sepsis groupings are based on clinical criteria such as the presence of shock, infection source, or organ failure, but such groupings may not represent the driving biology of the host response. They have also failed to adequately match patients for novel interventions. If the heterogeneity of sepsis truly reflects heterogeneity in the host response, characterization of these underlying host response types will be fundamental to enabling precision sepsis therapeutics (6).

In unsupervised analysis, data is sorted into subgroups ('clusters') that are defined only internally and without reference to external 'supervisory' outcomes, such as mortality or severity. Instead, the structure inherent within the data is used to define the subgroups. Such data-driven analyses have been successful in defining validated, clinically relevant disease subtypes in multiple diseases (4, 5, 7, 8). Since whole-blood gene expression reflects the temporal state of the circulating leukocytes, at least two academic groups have applied unsupervised clustering to whole-blood transcriptomic profiles in patients with sepsis to study the 'host response' in a data-driven framework(9-13). Their results have identified higher-mortality subtypes with evidence of immune exhaustion and diminished glucocorticoid receptor signaling, as well as lower-mortality subtypes with conventional pro-inflammatory signaling(9-13).

Clustering analyses often yield non-reproducible results for one of two reasons: either multiple arbitrary choices in methodology are used such that minor changes in analysis yield new results, or the clustered dataset is too small and not representative of the broad heterogeneity of a disease. However, recent advances in meta-clustering and data pooling can help solve both problems(14-16). Coupled with an unprecedented amount of publicly available transcriptomic data in sepsis (17, 18), the hypothesis that there exist robust, reproducible sepsis host-response subtypes (clusters) across the broad, heterogeneous spectrum of clinical sepsis was tested.

SUMMARY

Based on transcriptomic data, a subject that has sepsis can be assigned to one of three clusters: an "Inflammopathic"

cluster that is associated with a high innate immune/reduced adaptive immune signal, an "Adaptive" cluster that is associated with a reduced innate immune/high adaptive immune signal with low mortality, and a "Coagulopathic" one cluster that shows both clinical and molecular irregularities in the coagulation and complement systems.

In some embodiments, a method for determining whether a subject having sepsis has an Inflammopathic phenotype, an Adaptive phenotype or a Coagulopathic phenotype is provided. In these embodiments, this method may comprise: (a) measuring the amount of RNA transcripts encoded by at least two of ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in a sample of RNA obtained from the subject, to obtain gene expression data; and (b) based on the gene expression data, providing a report indicating whether the subject has an Inflammopathic phenotype, an Adaptive phenotype or a Coagulopathic phenotype, wherein:

(i) increased ARG1, LCN2, LTF, and/or OLFM4 and/or decreased HLA-DMB indicates that the subject has an Inflammopathic phenotype;

(ii) increased YKT6, PDE4B, TWISTNB, BTN2A2, ZBTB33, PSMB9, CAMK4, TMEM19, SLC12A7, TP53BP1, PLEKHO1, SLC25A22, and/or FRS2 and/or decreased GADD45A, CD24, S100A12, and/or STX1A indicates that the subject has an Adaptive phenotype; and (iii) increased KCNMB4, CRISP2, HTRA1, and/or PPL and/or decreased RHBDF2, ZCCHC4, YKT6, DDX6, SENP5, RAPGEF1, DTX2 and/or RELB indicates that the subject has a Coagulopathic phenotype.

In some embodiments, a method for treating a subject having sepsis. In these embodiments, the method may comprise:

(a) receiving a report indicating whether the subject has an Inflammopathic phenotype, an Adaptive phenotype or a Coagulopathic phenotype, wherein the report is based on the gene expression data obtained by measuring the amount of RNA transcripts encoded by at least two of ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in a sample of RNA obtained from the subject, wherein:

(i) increased ARG1, LCN2, LTF, and/or OLFM4 and/or decreased HLA-DMB indicates that the subject has an Inflammopathic phenotype;

(ii) increased YKT6, PDE4B, TWISTNB, BTN2A2, ZBTB33, PSMB9, CAMK4, TMEM19, SLC12A7, TP53BP1, PLEKHO1, SLC25A22, and/or FRS2 and/or decreased GADD45A, CD24, S100A12, and/or STX1A indicates that the subject has an Adaptive phenotype; and (iii) increased KCNMB4, CRISP2, HTRA1, and/or PPL and/or decreased RHBDF2, ZCCHC4, YKT6, DDX6, SENP5, RAPGEF1, DTX2 and/or RELB indicates that the subject has a Coagulopathic phenotype; and

(b) treating a subject based on whether the subject is indicated as having an Inflammopathic phenotype, an Adaptive phenotype or a Coagulopathic phenotype.

Kits for performing the method are also provided.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

4 biological signal at this number of clusters. Red arrow shows chosen clustering (stable K [3] at lowest number of genes [500]).

Figure 7:
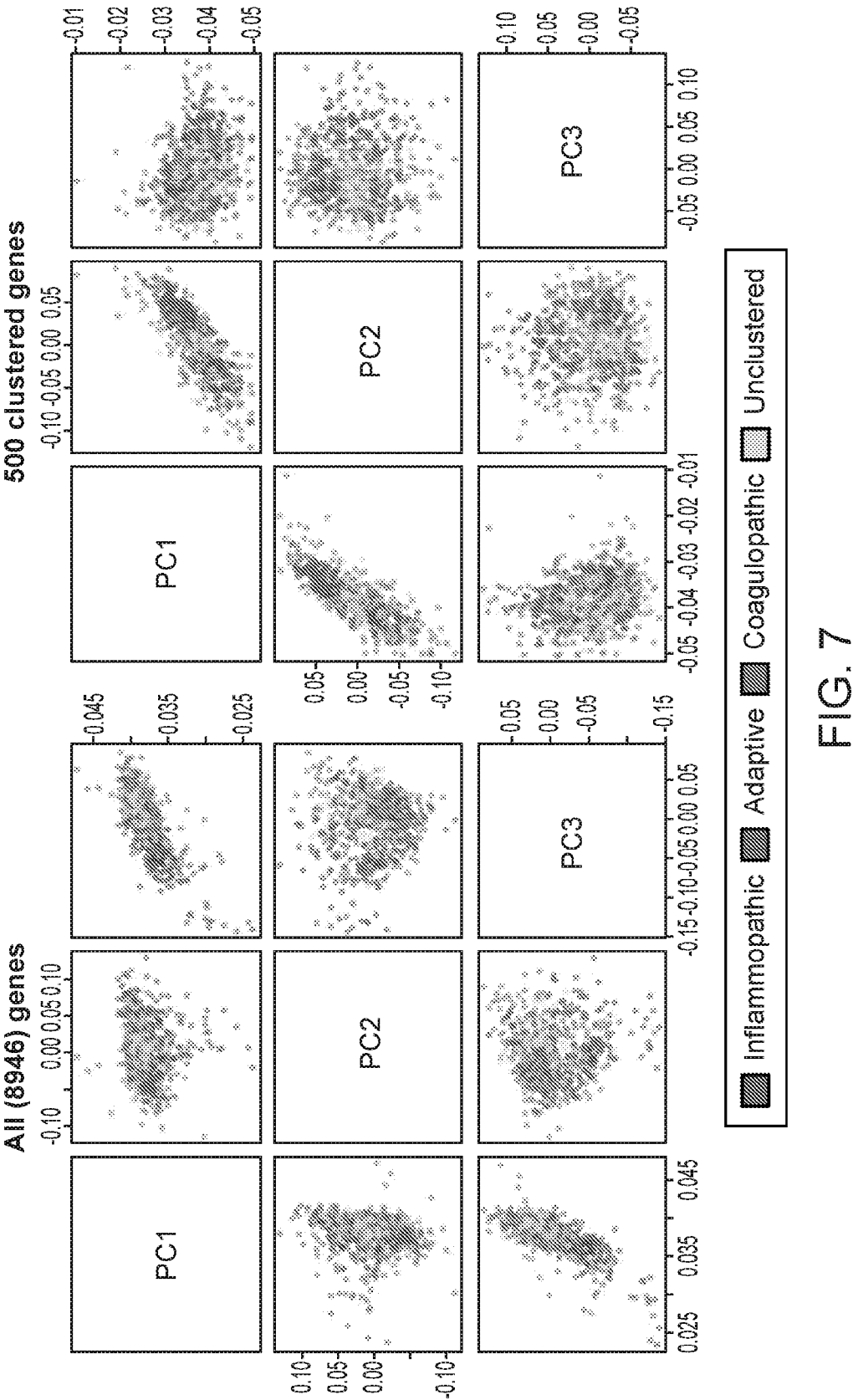

FIG. 7 depicts the Principal Components Analysis (PCA) of the discovery clustering results (including the 16% of samples that went unclustered in the final analysis, in gold) using either all 8,946 genes present in the COCONUT conormalized data, or only the 500 genes actually used in the clustering analysis. PCA is an unsupervised dimensionality reduction technique that allows for the visualization of high-dimensional data. Here it is shown that the cluster assignments that were recovered in an unsupervised manner are clearly separated in high-dimensional space, as demonstrated by the first three principal components. Adaptive samples appear to separate from Inflammopathic and Coagulopathic samples along PCs 1 and 2, while PC3 largely separates the Inflammopathic and Coagulopathic samples.

Figure 8:
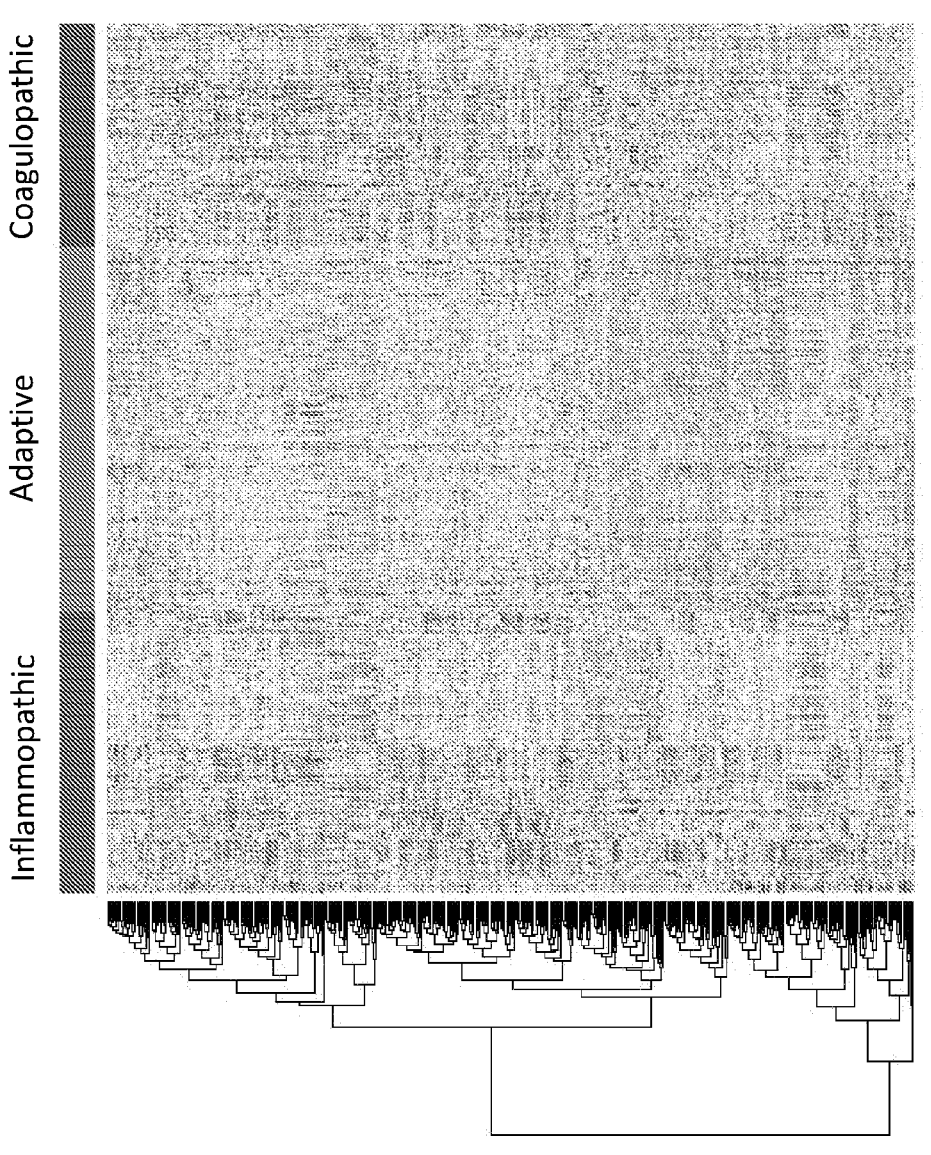

FIG. 8 depicts a heatmap of the 500 genes included in the clustering analysis for the discovery clusters, with hierarchical clustering of the genes solely for visualization.

Figure 9:
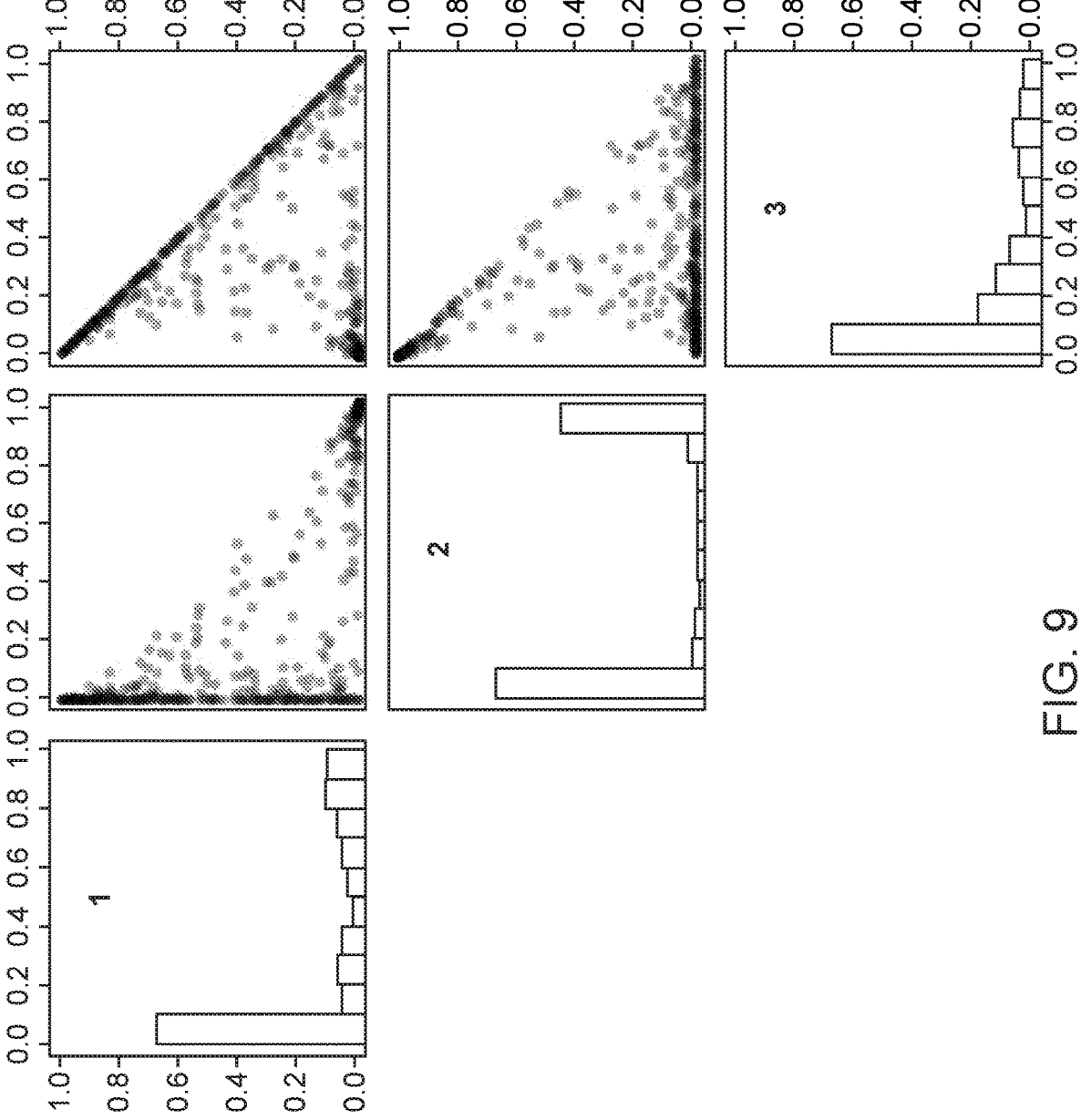

FIG. 9 depicts the comparison of raw predicted probability of cluster assignment in the discovery data. Histograms of probability show clear decision by the model for Adaptive, but Inflammopathic and Coagulopathic have less predicted certainty.

DETAILED DESCRIPTION

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that, as used in this specification and the appended claims, the singular forms "a", "an" and "the" include plural referents unless the content clearly dictates otherwise. Thus, for example, reference to "an agonist" includes a mixture of two or more such agonists, and the like.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Diagnostic Methods

As noted above, a method for determining whether a subject having sepsis (i.e., a subject that has been diagnosed as having sepsis or a subject that has sepsis that has not yet been diagnosed) has an Inflammopathic phenotype, an Adaptive phenotype or a Coagulopathic phenotype is provided. In some embodiments, the method may comprise:

(a) measuring the amount of RNA transcripts encoded by at least two of (e.g., at least 2, at least 3, at least 5, at least 10, at least 15, at least 20, at least 30 or all of) ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in a sample of RNA obtained from the subject, to obtain gene expression data; and (b) based on the gene expression data, providing a report indicating whether the subject has an Inflammopathic phenotype, an Adaptive phenotype or a Coagulopathic phenotype, wherein:

(i) increased ARG1, LCN2, LTF, and/or OLFM4 and/or decreased HLA-DMB indicates that the subject has an Inflammopathic phenotype;

(ii) increased YKT6, PDE4B, TWISTNB, BTN2A2, ZBTB33, PSMB9, CAMK4, TMEM19, SLC12A7, TP53BP1, PLEKHO1, SLC25A22, and/or FRS2 and/or decreased GADD45A, CD24, S100A12, and/or STX1A indicates that the subject has an Adaptive phenotype; and (iii) increased KCNMB4, CRISP2, HTRA1, and/or PPL and/or decreased RHBDF2, ZCCHC4, YKT6, DDX6, SENP5, RAPGEF1, DTX2 and/or RELB indicates that the subject has a Coagulopathic phenotype.

The measuring step can be done using any suitable method. For example, the amount of the RNA transcripts in the sample may be measured by RNA-seq (see, e.g., Morin et al BioTechniques 2008 45: 81-94; Wang et al 2009 Nature Reviews Genetics 10: 57-63), RT-PCR (Freeman et al Bio- Techniques 1999 26: 112-22, 124-5), or by labeling the RNA or cDNA made from the same and hybridizing the labeled RNA or cDNA to an array. An array may contain spatially-addressable or optically-addressable sequence-specific oligonucleotide probes that specifically hybridize to transcripts being measured, or cDNA made from the same. Spatially-addressable arrays (which are commonly referred to as "microarrays" in the art) are described in, e.g., Sealfon et al (see, e.g., Methods Mol Biol. 2011; 671:3-34). Optically-addressable arrays (which are commonly referred to as "bead arrays" in the art) use beads that internally dyed with fluorophores of differing colors, intensities and/or ratios such that the beads can be distinguished from each other, where the beads are also attached to an oligonucleotide probe. Exemplary bead-based assays are described in Dupont et al (J. Reprod Immunol. 2005 66:175-91) and Khalifian et al (J Invest Dermatol. 2015 135: 1-5). The abundance of transcripts in a sample can also be analyzed by quantitative RT-PCR or isothermal amplification method such as those described in Gao et al (J. Virol Methods. 2018 255: 71-75), Pease et al (Biomed Microdevices (2018) 20: 56) or Nixon et (Biomol. Det. and Quant 2014 2: 4-10), for example. Many other methods for measuring the amount of an RNA transcript in a sample are known in the art.

The sample of RNA obtained from the subject may comprise RNA isolated from whole blood, white blood cells, neutrophils or buffy coat, for example. Methods for making total RNA, polyA+ RNA, RNA that has been depleted for abundant transcripts, and RNA that has been enriched for the transcripts being measured are well known (see, e.g., Hitchen et al J Biomol Tech. 2013 24: S43-S44). If the method involves making cDNA from the RNA, then the cDNA may be made using an oligo(d)T primer, a random primer or a population of gene-specific primers that hybridize to the transcripts being analyzed.

In measuring the transcript, the absolute amount of each transcript may be determined, or the amount of each transcript relative to one or more control transcript may be determined. Whether the amount of a transcript is increased or decreased may be in relation to the amount of the transcript (e.g., the average amount of the transcript) in control samples (e.g., in blood samples collected from a population of at least 100, at least 200, or at least 500 subjects that have sepsis).

In some embodiments, the method may comprise providing a report indicating whether the subject has an Inflammopathic phenotype, an Adaptive phenotype or a Coagulopathic phenotype based on the measurements of the amounts of the transcripts. In some embodiments, this step may involve calculating three scores (one for each phenotype) based on the weighted amounts of each of the transcripts, where the scores correlates with the phenotype and can be a number such as a probability, likelihood or score out of 10, for example. In these embodiments, the method may comprise inputting the amounts of each of the transcripts into one or more algorithms, executing the algorithms, and receiving a score for each phenotype based on the calculations. In these embodiments, other measurements from the subject, e.g., whether the subject is male, the age of the subject, white blood cell count, neutrophils count, band count, lymphocyte count, monocyte count, whether the subject is immunosuppressed, and/or whether there are Gram-negative bacteria present, etc., may be input into the algorithm.

In some embodiments, the method may involve creating a report that shows the inflammatory age of the subject, e.g., in an electronic form, and forwarding the report to a doctor or other medical professional to help identify a suitable course of action, e.g., to identify a suitable therapy for the subject. The report may be used along with other metrics as a diagnostic to determine whether the subject has a disease or condition.

In any embodiment, report can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the report may be analyzed by an MD or other qualified medical professional, and a report based on the results of the analysis of the image may be forwarded to the subject from which the sample was obtained.

In computer-related embodiments, a system may include a computer containing a processor, a storage component (i.e., memory), a display component, and other components typically present in general purpose computers. The storage component stores information accessible by the processor, including instructions that may be executed by the processor and data that may be retrieved, manipulated or stored by the processor.

The storage component includes instructions for determining whether the subject has an Inflammopathic phenotype, an Adaptive phenotype or a Coagulopathic phenotype inflammatory using the measurements described above as inputs. The computer processor is coupled to the storage component and configured to execute the instructions stored in the storage component in order to receive patient data and analyze patient data according to one or more algorithms. The display component may display information regarding the diagnosis of the patient.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the diagnostic system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

Therapeutic Methods

Therapeutic methods are also provided. In some embodiments, these methods may comprise identifying a subject as having a phenotype using the methods described above, and treating a subject based on whether the subject is indicated as having an Inflammopathic phenotype, an Adaptive phenotype or a Coagulopathic phenotype. In some embodiments, the method may be a method for treating a subject having sepsis. In these embodiments, the method may comprise (a) receiving a report indicating whether the subject has an Inflammopathic phenotype, an Adaptive phenotype or a Coagulopathic phenotype, wherein the report is based on the gene expression data obtained by measuring the amount of RNA transcripts encoded by at least two of (e.g., at least 2, at least 3, at least 5, at least 10, at least 15, at least 20, at least 30 or all of) ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in a sample of RNA obtained from the subject, wherein:

(i) increased ARG1, LCN2, LTF, and/or OLFM4 and/or decreased HLA-DMB indicates that the subject has an Inflammopathic phenotype;

(ii) increased YKT6, PDE4B, TWISTNB, BTN2A2, ZBTB33, PSMB9, CAMK4, TMEM19, SLC12A7, TP53BP1, PLEKHO1, SLC25A22, and/or FRS2 and/or decreased GADD45A, CD24, S100A12, and/or STX1A indicates that the subject has an Adaptive phenotype; and (iii) increased KCNMB4, CRISP2, HTRA1, and/or PPL and/or decreased RHBDF2, ZCCHC4, YKT6, DDX6, SENP5, RAPGEF1, DTX2 and/or RELB indicates that the subject has a Coagulopathic phenotype; and (b) treating a subject based on whether the subject is indicated as having an Inflammopathic phenotype, an Adaptive phenotype or a Coagulopathic phenotype.

In some embodiments, the therapeutic method may comprise (a) measuring or having measured the amount of RNA transcripts encoded by at least two of ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in a sample of RNA obtained from the subject, to obtain gene expression data;

(b) identifying the subject as having an Inflammopathic phenotype, an Adaptive phenotype or a Coagulopathic phenotype based on the gene expression data, wherein:

(i) increased ARG1, LCN2, LTF, and/or OLFM4 and/or decreased HLA-DMB indicates that the subject has an Inflammopathic phenotype;

(ii) increased YKT6, PDE4B, TWISTNB, BTN2A2, ZBTB33, PSMB9, CAMK4, TMEM19, SLC12A7, TP53BP1, PLEKHO1, SLC25A22, and/or FRS2 and/or decreased GADD45A, CD24, S100A12, and/or STX1A indicates that the subject has an Adaptive phenotype; and (iii) increased KCNMB4, CRISP2, HTRA1, and/or PPL and/or decreased RHBDF2, ZCCHC4, YKT6, DDX6, SENP5, RAPGEF1, DTX2 and/or RELB indicates that the subject has a Coagulopathic phenotype; and (c) treating the patient accordingly, as described below. The treatment may be different depending on whether the subject is indicated as having an Inflammopathic phenotype, an Adaptive phenotype or a Coagulopathic phenotype.

For example, a subject indicated as having an Inflammopathic or Adaptive phenotype may be treated with an innate or adaptive immunity modulator such as abatacept, Abetimus, Abrilumab, adalimumab, Afelimomab, Aflibercept, Alefacept, anakinra, Andecaliximab, Anifrolumab, Anrukinzumab, Anti-lymphocyte globulin, Anti-thymocyte globulin, antifolate, Apolizumab, Apremilast, Aselizumab, Atezolizumab, Atorolimumab, Avelumab, azathioprine, Basiliximab, Belatacept, Belimumab, Benralizumab, Bertilimumab, Besilesomab, Bleselumab, Blisibimod, Brazikumab, Briakinumab, Brodalumab, Canakinumab, Carlumab, Cedelizumab, Certolizumab pegol, chloroquine, Clazakizumab, Clenoliximab, corticosteroids, cyclosporine, Daclizumab, Dupilumab, Durvalumab, Eculizumab, Efalizumab, Eldelumab, Elsilimomab, Emapalumab, Enokizumab, Epratuzumab, Erlizumab, etanercept, Etrolizumab, Everolimus, Fanolesomab, Faralimomab, Fezakinumab, Fletikumab, Fontolizumab, Fresolimumab, Galiximab, Gavilimomab, Gevokizumab, Gilvetmab, golimumab, Gomiliximab, Guselkumab, Gusperimus, hydroxychloroquine, Ibalizumab, Immunoglobulin E, Inebilizumab, infliximab, Inolimomab, Integrin, Interferon, Ipilimumab, Itolizumab, Ixekizumab, Keliximab, Lampalizumab, Lanadelumab, Lebrikizumab, leflunomide, Lemalesomab, Lenalidomide, Lenzilumab, Lerdelimumab, Letolizumab, Ligelizumab, Lirilumab, Lulizumab pegol, Lumiliximab, Maslimomab, Mavrilimumab, Mepolizumab, Metelimumab, methotrexate, minocycline, Mogamulizumab, Morolimumab, Muromonab-CD3, Mycophenolic acid, Namilumab, Natalizumab, Nerelimomab, Nivolumab, Obinutuzumab, Ocrelizumab, Odulimomab, Oleclumab, Olokizumab, Omalizumab, Otelixizumab, Oxelumab, Ozoralizumab, Pamrevlumab, Pascolizumab, Pateclizumab, PDE4 inhibitor, Pegsunercept, Pembrolizumab, Perakizumab, Pexelizumab, Pidilizumab, Pimecrolimus, Placulumab, Plozalizumab, Pomalidomide, Priliximab, purine synthesis inhibitors, pyrimidine synthesis inhibitors, Quilizumab, Reslizumab, Ridaforolimus, Rilonacept, rituximab, Rontalizumab, Rovelizumab, Ruplizumab, Samalizumab, Sarilumab, Secukinumab, Sifalimumab, Siplizumab, Sirolimus, Sirukumab, Sulesomab, sulfasalazine, Tabalumab, Tacrolimus, Talizumab, Telimomab aritox, Temsirolimus, Teneliximab, Teplizumab, Teriflunomide, Tezepelumab, Tildrakizumab, tocilizumab, tofacitinib, Toralizumab, Tralokinumab, Tregalizumab, Tremelimumab, Ulocuplumab, Umirolimus, Urelumab, Ustekinumab, Vapaliximab, Varlilumab, Vatelizumab, Vedolizumab, Vepalimomab, Visilizumab, Vobarilizumab, Zanolimumab, Zolimomab aritox, Zotarolimus, or recombinant human cytokines, such as rh-interferon-gamma.

In another example, a subject indicated as having Inflammopathic or Adaptive phenotype may be treated with a blockade or signaling modification of PD1, PDL1, CTLA4, TIM-3, BTLA, TREM-1, LAGS, VISTA, or any of the human clusters of differentiation, including CD1, CD1a, CD1b, CD1c, CD1d, CD1e, CD2, CD3, CD3d, CD3e, CD3g, CD4, CD5, CD6, CD7, CD8, CD8a, CD8b, CD9, CD10, CD11a, CD11b, CD11c, CD11d, CD13, CD14, CD15, CD16, CD16a, CD16b, CD17, CD18, CD19, CD20, CD21, CD22, CD23, CD24, CD25, CD26, CD27, CD28, CD29, CD30, CD31, CD32A, CD32B, CD33, CD34, CD35, CD36, CD37, CD38, CD39, CD40, CD41, CD42, CD42a, CD42b, CD42c, CD42d, CD43, CD44, CD45, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64a, CD65, CD65s, CD66a, CD66b, CD66c, CD66d, CD66e, CD66f, CD68, CD69, CD70, CD71, CD72, CD73, CD74, CD75, CD75s, CD77, CD79A, CD79B, CD80, CD81, CD82, CD83, CD84, CD85A, CD85B, CD85C, CD85D, CD85F, CD85G, CD85H, CD85I, CD85J, CD85K, CD85M, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD107a, CD107b, CD108, CD109, CD110, CD111, CD112, CD113, CD114, CD115, CD116, CD117, CD118, CD119, CD120, CD120a, CD120b, CD121a, CD121b, CD122, CD123, CD124, CD125, CD126, CD127, CD129, CD130, CD131, CD132, CD133, CD134, CD135, CD136, CD137, CD138, CD139, CD140A, CD140B, CD141, CD142, CD143, CD144, CDw145, CD146, CD147, CD148, CD150, CD151, CD152, CD153, CD154, CD155, CD156, CD156a, CD156b, CD156c, CD157, CD158, CD158A, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD187, CD188, CD189, CD190, CD191, CD192, CD193, CD194, CD195, CD196, CD197, CDw198, CDw199, CD200, CD201, CD202b, CD203c, CD204, CD205, CD206, CD207, CD208, CD209, CD210, CDw210a, CDw210b, CD211, CD212, CD213a1, CD213a2, CD214, CD215, CD216, CD217, CD218a, CD218b, CD219, CD220, CD221, CD222, CD223, CD224, CD225, CD226, CD227, CD228, CD229, CD230, CD231, CD232, CD233, CD234, CD235a, CD235b, CD236, CD237, CD238, CD239, CD240CE, CD240D, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CDw293, CD294, CD295, CD296, CD297, CD298, CD299, CD300A, CD300C, CD301, CD302, CD303, CD304, CD305, CD306, CD307, CD307a, CD307b, CD307c, CD307d, CD307e, CD308, CD309, CD310, CD311, CD312, CD313, CD314, CD315, CD316, CD317, CD318, CD319, CD320, CD321, CD322, CD323, CD324, CD325, CD326, CD327, CD328, CD329, CD330, CD331, CD332, CD333, CD334, CD335, CD336, CD337, CD338, CD339, CD340, CD344, CD349, CD351, CD352, CD353, CD354, CD355, CD357, CD358, CD360, CD361, CD362, CD363, CD364, CD365, CD366, CD367, CD368, CD369, CD370, or CD371.

In another example, a subject indicated as having a Coagulopathic phenotype may be treated with one or more drugs that modify the coagulation cascade or platelet activation, such as those targeting Albumin, Antihemophilic globulin, AHF A, C1-inhibitor, Ca++, CD63, Christmas factor, AHF B, Endothelial cell growth factor, Epidermal growth factor, Factors V, XI, XIII, Fibrin-stabilizing factor, Laki-Lorand factor, fibrinase, Fibrinogen, Fibronectin, GMP 33, Hageman factor, High-molecular-weight kininogen, IgA, IgG, IgM, Interleukin-1B, Multimerin, P-selectin, Plasma thromboplastin antecedent, AHF C, Plasminogen activator inhibitor 1, Platelet factor, Platelet-derived growth factor, Prekallikrein, Proaccelerin, Proconvertin, Protein C, Protein M, Protein S, Prothrombin, Stuart-Prower factor, TF, thromboplastin, Thrombospondin, Tissue factor pathway inhibitor, Transforming growth factor-β, Vascular endothelial growth factor, Vitronectin, von Willebrand factor, α2-Antiplasmin, α2-Macroglobulin, β-Thromboglobulin, or other members of the coagulation or platelet-activation cascades.

In another example, a subject having a Coagulopathic phenotype may treated with a blood product, heparin, low-molecular-weight heparin, apixaban, dabigatran, rivaroxaban, dalteparin, fondaparinux, warfarin, activated protein C, recombinant coagulation cascade proteins, tranexamic acid, or another coagulation-modifying drug.

Methods for administering and dosages for administering the therapeutics listed above are known in the art or can be derived from the art.

In some embodiments, the subject may also be treated for sepsis. For example, the patent also may be treated with a broad spectrum antibiotic, e.g., meropenem, imipenem, piperacillin-tazobactam, or tigecycline, or a combination therapy that includes metronidazole plus either levofloxacin, aztreonam, cefepime, or ceftriaxone, in addition to a compound listed above.

Kits

Also provided by this disclosure are kits for practicing the subject methods, as described above. In some embodiments, the kit may reagents for measuring the amount of RNA transcripts encoded by at least 2, at least 3, at least 5, at least 10, at least 15, at least 20, at least 30 or all of ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB. In some embodiments, the kit may comprise, for each RNA transcript, a sequence-specific oligonucleotide that hybridizes to the transcript. In some embodiments, the sequence-specific oligonucleotide may be biotinylated and/or labeled with an optically-detectable moiety. In some embodiments, the kit may comprise, for each RNA transcript, a pair of PCR primers that amplify a sequence from the RNA transcript, or cDNA made from the same. In some embodiments, the kit may comprise an array of oligonucleotide probes, wherein the array comprises, for each RNA transcript, at least one sequence-specific oligonucleotide that hybridizes to the transcript. The oligonucleotide probes may be spatially addressable on the surface of a planar support, or tethered to optically addressable beads, for example.

The various components of the kit may be present in separate containers or certain compatible components may be precombined into a single container, as desired.

In addition to the above-mentioned components, the subject kit may further include instructions for using the components of the kit to practice the subject method.

Embodiments

1. A method for determining whether a subject having sepsis has an Inflammopathic phenotype, an Adaptive phenotype or a Coagulopathic phenotype, comprising:
   (a) measuring the amount of RNA transcripts encoded by at least two of ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in a sample of RNA obtained from the subject, to obtain gene expression data; and
   (b) based on the gene expression data, providing a report indicating whether the subject has an Inflammopathic phenotype, an Adaptive phenotype or a Coagulopathic phenotype, wherein:
   (i) increased ARG1, LCN2, LTF, and/or OLFM4 and/or decreased HLA-DMB indicates that the subject has an Inflammopathic phenotype;
   (ii) increased YKT6, PDE4B, TWISTNB, BTN2A2, ZBTB33, PSMB9, CAMK4, TMEM19, SLC12A7, TP53BP1, PLEKHO1, SLC25A22, and/or FRS2 and/or decreased GADD45A, CD24, S100A12, and/or STX1A indicates that the subject has an Adaptive phenotype; and
   (iii) increased KCNMB4, CRISP2, HTRA1, and/or PPL and/or decreased RHBDF2, ZCCHC4, YKT6, DDX6, SENP5, RAPGEF1, DTX2 and/or RELB indicates that the subject has a Coagulopathic phenotype.

2. The method of embodiment 1, wherein the measuring step is done by sequencing.

3. The method of embodiment 1, wherein the measuring step is done by RT-PCR.

4. The method of embodiment 1, wherein the measuring step is done by labeling the RNA or cDNA made from the same and hybridizing the labeled RNA or cDNA to a support, e.g., an array or beads.

5. The method of any prior embodiment, wherein the sample comprises RNA isolated from whole blood, white blood cells, neutrophils or buffy coat.

6. A method for treating a subject having sepsis, comprising:
   (a) receiving a report indicating whether the subject has an Inflammopathic phenotype, an Adaptive phenotype or a Coagulopathic phenotype, wherein the report is based on the gene expression data obtained by measuring the amount of RNA transcripts encoded by at least two of ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in a sample of RNA obtained from the subject, wherein:

(i) increased ARG1, LCN2, LTF, and/or OLFM4 and/or decreased HLA-DMB indicates that the subject has an Inflammopathic phenotype;

(ii) increased YKT6, PDE4B, TWISTNB, BTN2A2, ZBTB33, PSMB9, CAMK4, TMEM19, SLC12A7, TP53BP1, PLEKHO1, SLC25A22, and/or FRS2 and/or decreased GADD45A, CD24, S100A12, and/or STX1A indicates that the subject has an Adaptive phenotype; and (iii) increased KCNMB4, CRISP2, HTRA1, and/or PPL and/or decreased RHBDF2, ZCCHC4, YKT6, DDX6, SENP5, RAPGEF1, DTX2 and/or RELB indicates that the subject has a Coagulopathic phenotype; and (b) treating the subject based on whether the subject is indicated as having an Inflammopathic phenotype, an Adaptive phenotype or a Coagulopathic phenotype.

7. The method of embodiment 6, wherein a subject having an Inflammopathic or Adaptive phenotype is treated with an innate or adaptive immunity modulator such as abatacept, Abetimus, Abrilumab, adalimumab, Afelimomab, Aflibercept, Alefacept, anakinra, Andecaliximab, Anifrolumab, Anrukinzumab, Anti-lymphocyte globulin, Anti-thymocyte globulin, antifolate, Apolizumab, Apremilast, Aselizumab, Atezolizumab, Atorolimumab, Avelumab, azathioprine, Basiliximab, Belatacept, Belimumab, Benralizumab, Bertilimumab, Besilesomab, Bleselumab, Blisibimod, Brazikumab, Briakinumab, Brodalumab, Canakinumab, Carlumab, Cedelizumab, Certolizumab pegol, chloroquine, Clazakizumab, Clenoliximab, corticosteroids, cyclosporine, Daclizumab, Dupilumab, Durvalumab, Eculizumab, Efalizumab, Eldelumab, Elsilimomab, Emapalumab, Enokizumab, Epratuzumab, Erlizumab, etanercept, Etrolizumab, Everolimus, Fanolesomab, Faralimomab, Fezakinumab, Fletikumab, Fontolizumab, Fresolimumab, Galiximab, Gavilimomab, Gevokizumab, Gilvetmab, golimumab, Gomiliximab, Guselkumab, Gusperimus, hydroxychloroquine, Ibalizumab, Immunoglobulin E, Inebilizumab, infliximab, Inolimomab, Integrin, Interferon, Ipilimumab, Itolizumab, Ixekizumab, Keliximab, Lampalizumab, Lanadelumab, Lebrikizumab, leflunomide, Lemalesomab, Lenalidomide, Lenzilumab, Lerdelimumab, Letolizumab, Ligelizumab, Lirilumab, Lulizumab pegol, Lumiliximab, Maslimomab, Mavrilimumab, Mepolizumab, Metelimumab, methotrexate, minocycline, Mogamulizumab, Morolimumab, Muromonab-CD3, Mycophenolic acid, Namilumab, Natalizumab, Nerelimomab, Nivolumab, Obinutuzumab, Ocrelizumab, Odulimomab, Oleclumab, Olokizumab, Omalizumab, Otelixizumab, Oxelumab, Ozoralizumab, Pamrevlumab, Pascolizumab, Pateclizumab, PDE4 inhibitor, Pegsunercept, Pembrolizumab, Perakizumab, Pexelizumab, Pidilizumab, Pimecrolimus, Placulumab, Plozalizumab, Pomalidomide, Priliximab, purine synthesis inhibitors, pyrimidine synthesis inhibitors, Quilizumab, Reslizumab, Ridaforolimus, Rilonacept, rituximab, Rontalizumab, Rovelizumab, Ruplizumab, Samalizumab, Sarilumab, Secukinumab, Sifalimumab, Siplizumab, Sirolimus, Sirukumab, Sulesomab, sulfasalazine, Tabalumab, Tacrolimus, Talizumab, Telimomab aritox, Temsirolimus, Teneliximab, Teplizumab, Teriflunomide, Tezepelumab, Tildrakizumab, tocilizumab, tofacitinib, Toralizumab, Tralokinumab, Tregalizumab, Tremelimumab, Ulocuplumab, Umirolimus, Urelumab, Ustekinumab, Vapaliximab, Varlilumab, Vatelizumab, Vedolizumab, Vepalimomab, Visilizumab, Vobarilizumab, Zanolimumab, Zolimomab aritox, Zotarolimus, or recombinant human cytokines, such as rh-interferon-gamma.

8. The method of embodiment 6, wherein a subject having an Inflammopathic or Adaptive phenotype is treated with a blockade or signaling modification of PD1, PDL1, CTLA4, TIM-3, BTLA, TREM-1, LAG3, VISTA, or any of the human clusters of differentiation, including CD1, CD1a, CD1b, CD1c, CD1d, CD1e, CD2, CD3, CD3d, CD3e, CD3g, CD4, CD5, CD6, CD7, CD8, CD8a, CD8b, CD9, CD10, CD11a, CD11b, CD11c, CD11d, CD13, CD14, CD15, CD16, CD16a, CD16b, CD17, CD18, CD19, CD20, CD21, CD22, CD23, CD24, CD25, CD26, CD27, CD28, CD29, CD30, CD31, CD32A, CD32B, CD33, CD34, CD35, CD36, CD37, CD38, CD39, CD40, CD41, CD42, CD42a, CD42b, CD42c, CD42d, CD43, CD44, CD45, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64a, CD65, CD65s, CD66a, CD66b, CD66c, CD66d, CD66e, CD66f, CD68, CD69, CD70, CD71, CD72, CD73, CD74, CD75, CD75s, CD77, CD79A, CD79B, CD80, CD81, CD82, CD83, CD84, CD85A, CD85B, CD85C, CD85D, CD85F, CD85G, CD85H, CD85I, CD85J, CD85K, CD85M, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD107a, CD107b, CD108, CD109, CD110, CD111, CD112, CD113, CD114, CD115, CD116, CD117, CD118, CD119, CD120, CD120a, CD120b, CD121a, CD121b, CD122, CD123, CD124, CD125, CD126, CD127, CD129, CD130, CD131, CD132, CD133, CD134, CD135, CD136, CD137, CD138, CD139, CD140A, CD140B, CD141, CD142, CD143, CD144, CDw145, CD146, CD147, CD148, CD150, CD151, CD152, CD153, CD154, CD155, CD156, CD156a, CD156b, CD156c, CD157, CD158, CD158A, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD187, CD188, CD189, CD190, CD191, CD192, CD193, CD194, CD195, CD196, CD197, CDw198, CDw199, CD200, CD201, CD202b, CD203c, CD204, CD205, CD206, CD207, CD208, CD209, CD210, CDw210a, CDw210b, CD211, CD212, CD213a1, CD213a2, CD214, CD215, CD216, CD217, CD218a, CD218b, CD219, CD220, CD221, CD222, CD223, CD224, CD225, CD226, CD227, CD228, CD229, CD230, CD231, CD232, CD233, CD234, CD235a, CD235b, CD236, CD237, CD238, CD239, CD240CE, CD240D, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CDw293, CD294, CD295, CD296, CD297, CD298, CD299, CD300A, CD300C, CD301, CD302, CD303, CD304, CD305, CD306, CD307, CD307a, CD307b, CD307c, CD307d, CD307e, CD308, CD309, CD310, CD311, CD312, CD313, CD314, CD315, CD316, CD317, CD318, CD319, CD320, CD321, CD322, CD323, CD324, CD325, CD326, CD327, CD328, CD329, CD330, CD331, CD332, CD333, CD334, CD335, CD336, CD337, CD338, CD339, CD340, CD344, CD349, CD351, CD352, CD353, CD354, CD355, CD357, CD358, CD360, CD361, CD362, CD363, CD364, CD365, CD366, CD367, CD368, CD369, CD370, or CD371.

9. The method of embodiment 6, wherein a subject having a Coagulopathic phenotype is treated with one or more drugs that modify the coagulation cascade or platelet activation, such as those targeting Albumin, Antihemophilic globulin, AHF A, C1-inhibitor, Ca++, CD63, Christmas factor, AHF B, Endothelial cell growth factor, Epidermal growth factor, Factors V, XI, XIII, Fibrin-stabilizing factor, Laki-Lorand factor, fibrinase, Fibrinogen, Fibronectin, GMP 33, Hageman factor, High-molecular-weight kininogen, IgA, IgG, IgM, Interleukin-1B, Multimerin, P-selectin, Plasma thromboplastin antecedent, AHF C, Plasminogen activator inhibitor 1, Platelet factor, Platelet-derived growth factor, Prekallikrein, Proaccelerin, Proconvertin, Protein C, Protein M, Protein S, Prothrombin, Stuart-Prower factor, TF, thromboplastin, Thrombospondin, Tissue factor pathway inhibitor, Transforming growth factor-β, Vascular endothelial growth factor, Vitronectin, von Willebrand factor, α2-Antiplasmin, α2-Macroglobulin, β-Thromboglobulin, or other members of the coagulation or platelet-activation cascades.

10. The method of embodiment 6, wherein a subject having a Coagulopathic phenotype is treated with a blood product, heparin, low-molecular-weight heparin, apixaban, dabigatran, rivaroxaban, dalteparin, fondaparinux, warfarin, activated protein C, recombinant coagulation cascade proteins, tranexamic acid, or another coagulation-modifying drug.

11. The method of any prior embodiment, wherein the indication of whether the subject has an Inflammopathic phenotype, an Adaptive phenotype or a Coagulopathic phenotype is further based on whether the subject is male, the age of the subject, white blood cell count, neutrophils count, band count, lymphocyte count, monocyte count, whether the subject is immunosuppressed, and/or whether there are Gram-negative bacteria present.

12. A method comprising:
measuring the amount of RNA transcripts encoded by at least two of ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in a sample of RNA obtained from a subject.

13. The method of any prior embodiment, wherein the gene expression data comprises a measurement of the amount of RNA transcripts encoded by at least 3, at least 5, at least 10, at least 15, at least 20, at least 30 or all of ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in a sample of RNA obtained from a subject.

14. A kit comprising reagents for measuring the amount of RNA transcripts encoded by at least 2, at least 3, at least 5, at least 10, at least 15, at least 20, at least 30 or all of ARG1, LCN2, LTF, OLFM4, HLA-DMB, YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB.

15. The kit of embodiment 14, wherein the reagents comprise, for each RNA transcript, a sequence-specific oligonucleotide that hybridizes to the transcript.

16. The kit of embodiment 15, wherein sequence-specific oligonucleotide is biotinylated and/or labeled with an optically-detectable moiety.

17. The kit of embodiment 14, wherein the reagents comprises, for each RNA transcript, a pair of PCR primers that amplify a sequence from the RNA transcript, or cDNA made from the same.

18. The kit of embodiment 14, wherein the reagents comprise an array of oligonucleotide probes, wherein the array comprises, for each RNA transcript, at least one sequence-specific oligonucleotide that hybridizes to the transcript.

Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (pl); seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM); millimolar (mM); molar (M); amino acids (aa); kilobases (kb); base pairs (bp); nucleotides (nt); intramuscular (i.m.); intraperitoneal (i.p.); subcutaneous (s.c.); and the like.

SUMMARY

Sepsis may not be a single disease, but rather a spectrum composed of several 'endotypes' (also known as clusters, or subclasses of disease). It was hypothesized that there are sepsis clusters that exist broadly across patients with sepsis, and used transcriptomic data (gene expression microarray and RNAseq) from whole blood from a wide range of clinical settings to test this hypothesis.

A new bioinformatics method was published that relies on an assumption that healthy controls among different studies are largely the same. Using this assumption, data can be pooled in a bias-free manner (i.e., without assuming anything about the sepsis cases) from different studies into a single framework, and allow them to be analyzed as though they were gathered in a single large study. Thus, all transcriptomic studies of bacterial sepsis at hospital admission were gathered, and they were split into all studies with healthy controls (which was used for discovering sepsis clusters) and those without healthy controls (which was used as validation for the clusters found in discovery).

Across the discovery data (700 patients from 14 datasets), advanced bioinformatics was used to determine that the transcriptomic data was ideally split into 3 clusters. Pathway analysis was performed in the gene expression profiles of the subjects in the 3 clusters, and found that one cluster had a high innate immune/reduced adaptive immune signal ('Inflammopathic'), one cluster had a reduced innate immune/high adaptive immune signal with low mortality ('Adaptive'), and one cluster showed both clinical and molecular irregularities in the coagulation and complement systems ('Coagulopathic'). Cluster membership was associated with significantly different age, shock status, clinical severity, white blood cell differential, and mortality. However, the effect of age, shock status, and illness severity on cluster membership was characterized, and it was shown that they explain very little of why patients are assigned to the given clusters. This suggests that cluster membership is not simply explained by obvious clinical variables.

In order to ever have any clinical relevance, some way to determine cluster membership for any given new patient is needed. In other words, there is a need for some diagnostic blood test that determines cluster membership that could be run when a patient presents with sepsis. Thus, a 33-gene classifier in the discovery data that had an 83% accuracy in re-assigning discovery patients to their same clusters was derived. This 33-gene classifier was applied in 9 external, independent datasets (N=600), to retrospectively assign each of the 600 patients to one of the three clusters (Inflammopathic, Adaptive, or Coagulopathic).

Having retrospectively assigned these patients to the three clusters, it was necessary to determine whether they recapitulated the same clinical and biological characteristics as the original Inflammopathic, Adaptive, and Coagulopathic groups. it was shown that the same relative patterns of age, severity, shock, and mortality were found, on average, between the validation clusters and the discovery clusters. It was also shown that the same pathways were generally activated among patients across cohorts assigned to the same cluster.

Analysis shows that there are three different sepsis subtypes (Inflammopathic, Adaptive, and Coagulopathic). These subtypes have significantly different clinical and molecular profiles. The study also produced a 33-gene classifier which is able to identify any new patient as belonging to one of these clusters. The idea of an endotype has clinical use because it can be coupled with an endotype-specific therapy.

Methods

Systematic Search and Dataset Criteria

A systematic search of GEO and ArrayExpress for gene expression studies of clinical studies in sepsis, as previously described (16) was performed. Individual datasets were renormalized as previously described (18). Datasets were only included if they studied whole blood gene expression at hospital or ICU admission (i.e., primary admission for sepsis). Since the host response differs substantially between bacterial and viral infections(15, 19), an unsupervised analysis would likely lead to groupings primarily based on infection type. All samples with microbiologically confirmed viral infection were removed unless a microbiologically confirmed bacterial infection was also present (only 3 confirmed co-infections were included). Studies that did not supply sample-level microbiological data but were identified in their manuscript as being drawn from patients with primarily bacterial sepsis were treated as all bacterial. Patients that were sampled more than 48 hours after sepsis diagnosis were further removed given the potential impact of treatment on the host response(20, 21). All data used herein were de-identified and publicly available and so exempt from IRB review.

Pooling Data with COCONUT to Enable Clustering

The recent development of the COmbat CO-Normalization Using conTrols method (COCONUT)(15) allows for bias-free correction of batch effects between multiple microarray datasets, enabling pooled analysis, provided that healthy controls are present. The core assumption is that healthy controls across datasets come from the same statistical distribution. This assumption allows for the calculation of correction factors that remove technical differences across pooled datasets without bias to the number or type of diseased samples present.

The datasets were split into 'discovery' and 'validation' groups based on whether healthy controls were present in the dataset, specifically so that the COCONUT method could be used. Since the inclusion of healthy controls in any given dataset is essentially random, the discovery/validation split was not expected to introduce bias. The COCONUT method was used to co-normalize the discovery datasets into a single pool, and then removed all healthy controls from further analysis.

Clustering the Discovery Data Using COMMUNAL

In order to determine how many clusters were present in the COCONUT-conormalized discovery data, the COmbined Mapping of Multiple clUsteriNg ALgorithms (COMMUNAL) method was used, which integrates data from multiple clustering algorithms and validity metrics across a range of included variables to identify the most robust number of clusters present in the data (see Supplementary Materials and Methods and Supplementary Results) (14). The top 5,000 genes across the discovery datasets were ranked using an algorithm that accounts for both within-dataset variance and between-dataset variance (16). COMMUNAL was run using consensus-clustering versions of two algorithms, K-means clustering and Partitioning Around Medioids (PAM), due to their robustness in large, noisy datasets. Both methods were run across a range of variables from 100 genes up to 5,000 genes (in ranked order). COMMUNAL then integrated these data (at its default parameters) to produce an optimality map of clustering. In the resulting map, the most stable optima were taken as indicating the most robust clustering.

Having chosen an optimal clustering using COMMUNAL, the sample assignments were integrated between clustering algorithms (i.e., the clusters into which the PAM and K-means algorithms assigned samples). The COMMUNAL method assigned all samples for which the clustering algorithms agreed to discovery clusters, and removed all samples for which there was disagreement between the PAM and K-means methods as 'unclustered'. The hypothesis is that not every sample may be perfectly assigned to a given cluster (e.g., some samples may exhibit biology suggestive of two clusters). Since classifiers trained on data with fewer errors are more robust, removing these uncertain samples improves the classifier accuracy. Note that the classifier built for validation does not produce 'unclustered' assignments (see Supplementary Materials and Methods and Supplementary Results).

To check whether the discovery clusters appeared to be separated in gene expression space, they were visualized using both heat maps and principal component analyses. Pooled sample-level demographic and phenotypic data was used to investigate clinical differences between discovery clusters.

Biological and Clinical Investigations

The details of the treatment of complex clinical variables including illness severity, immunosuppression, and coagulopathy are explained in the Supplemental Materials and Methods and Supplemental Results sections below. Gene ontology analysis (22), the construction of a cluster classifier (23), and testing of the validation datasets are described in the Supplementary Materials and Methods and Supplementary Results.

Results

Included Studies, COCONUT Conormalization, and COMMUNAL Cluster Selection

Figure 1:
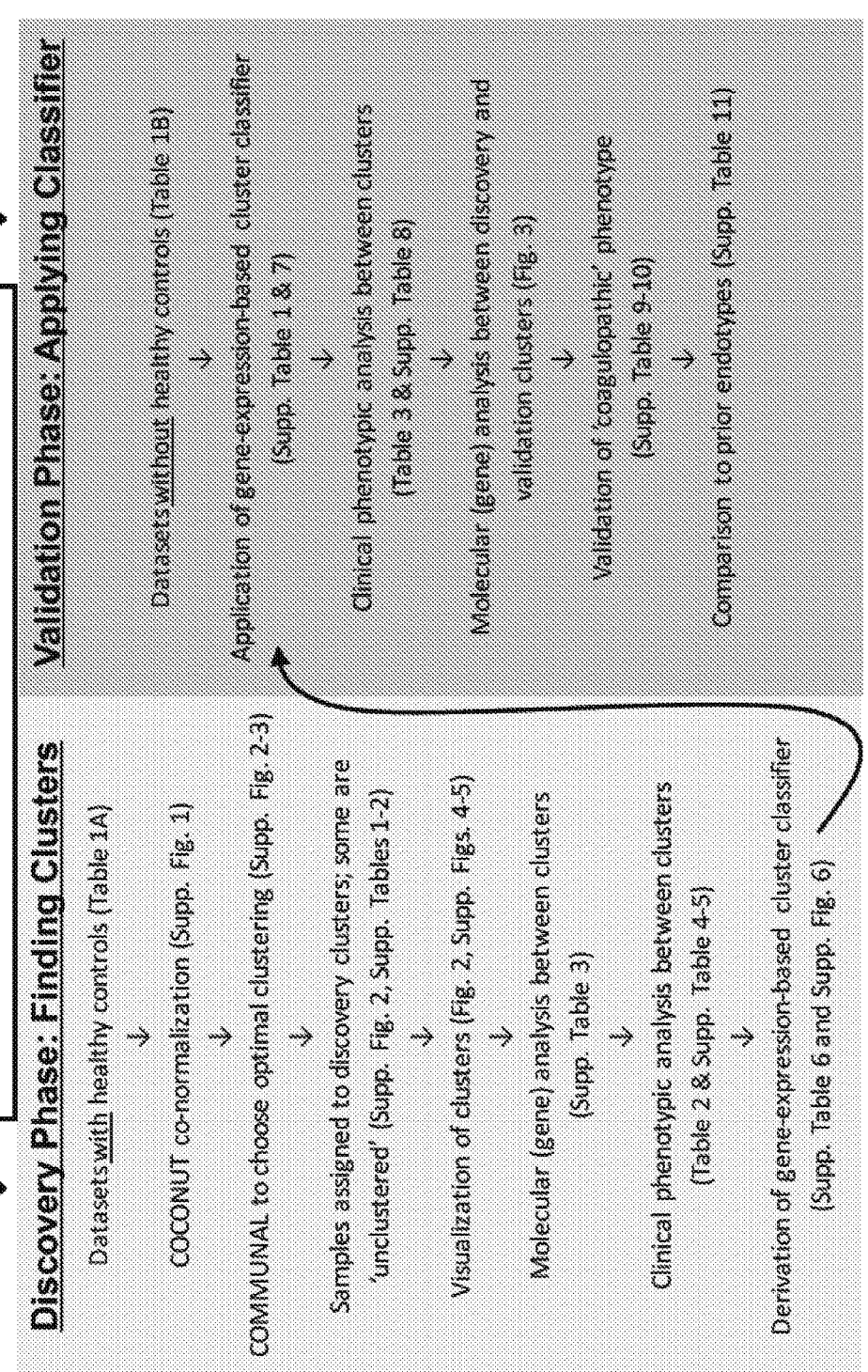
FIG. 1 depicts the overall study schematic.

It was first hypothesized that robust molecular subgroups exist in patients with bacterial sepsis. A unified clustering was performed across 14 bacterial sepsis discovery datasets from 8 different countries (N=700, Table 1a) using COCONUT co-normalization (24-37). 9 validation datasets were identified from 5 different countries that matched inclusion criteria but did not include healthy controls (N=600, Table 1b and FIG. 1)(12, 38-43).

TABLE 1

Datasets included in the study. (A) Datasets with healthy controls were chosen for discovery and (B) datasets without healthy controls were chosen for validation.

| Use | Accession | First author | Description of patients used here | Timing of sepsis diagnosis | Sample Size (N) | Age | Sex (percent male) | Severity | Mortality (percent) | Country |
|---|---|---|---|---|---|---|---|---|---|---|
| A. Discovery | EMEXP3567 | Irwin | Children with meningococcal sepsis +/- HIV co-infection | Admission to ED | 12 | 2.0 (IQR 0.6-6.9) | 55 | unk. | 50 | Malawi |
| | EMTAB1548 | Almansa | Adult surgical patients with sepsis (EXPRESS study) | Average post-operation day 4 (hospital acquired) | 82 | 69.7 (std. dev. 13.1) | 67 | APACHE II 17.0 (std. dev. 5.4) | 32 | Spain |
| | GSE11755 | Emonts | Children with meningococcal septic shock | Admission to ICU | 6 | 1.94 | 100 | PRISM 24 | 0 | Netherlands |
| | GSE13015 gpl6106 | Pankla | Adults with sepsis, many from burkholderia | Within 48 hours of diagnosis; both community-acquired and hospital-acquired. | 48 | 54.7 (std. dev. 11.7) | 54 | unk. | 27 | Thailand |
| | GSE13015 gpl6947 | | | | 15 | | | | 47 | |
| | GSE20346 | Parnell | Adults with severe bacterial pneumonia | Admission to ICU | 6 | 63 (range 52-75) | 50 | APACHE II 22 (range 10-33) | 33 | Australia |
| | GSE28750 | Sutherland | Community-acquired sepsis with bacteremia | Admission to ICU | 10 | 60 | 55 | unk | unk | Australia |
| | GSE33341 | Ahn | Adults with 2+ SIRS criteria and bacteremia | Within 24 hours of admission to hospital | 51 | 58 (range 24-91) | 61 | unk. | 4 | USA |
| | GSE40012 | Parnell | Adults in ICU with sepsis | Admission to ICU | 21 | 61 (std. dev. 16) | 40 | APACHE II 21 (std. dev. 6) | 26 | Australia |
| | GSE40586 | Lill | Infants, children, and adults with bacterial meningitis | Within 48 hours of hospital admission | 21 | 43.4 (range 17 d-70 y) | unk. | unk. | 10 | Estonia |
| | GSE57065 | Cazalis | Adults with septic shock | Within 48 hours of admission to ICU | 56 | 62 | 68 | SOFA 10.5 (IQR 9-13) | 18 | France |
| | GSE65682 | Scicluna | Adults with community-acquired pneumonia in ICU | Within 24 hours of ICU admission | 101 | 64 | 57 | APACHE IV 81 | 24 | Netherlands |
| | GSE66099 | Wong | Children in ICU with sepsis/septic shock | Admission to ICU | 188 | 3.7 | 58 | PRISM 15.7 | 14 | USA |
| | GSE69528 | Khaenam | Adults with sepsis, many from burkholderia | unknown | 83 | adults | unk | unk | unk | Thailand |

TABLE 1-continued

Datasets included in the study. (A) Datasets with healthy controls were chosen for
discovery and (B) datasets without healthy controls were chosen for validation.

| Use | Accession | First author | Description of patients used here | Timing of sepsis diagnosis | Sample Size (N) | Age | Sex (percent male) | Severity | Mortality (percent) | Country |
|-----|-----------|--------------|-----------------------------------|----------------------------|-----------------|-----|--------------------|----------|---------------------|---------|
| B. Validation | EMEXP3850 | Kwan | Children w/ meningococcal sepsis | Admission to hospital; sampled at multiple times 0-48 hrs | 24 | 1.3 (range 0.8-2.0) | 40 | PELOD; 29.2 (range 11-61) | 21 | UK |
| | EMTAB4421.51 | Davenport | Adults with sepsis (GAinS study) | Within 24 hours of admission to ICU | 178 | 64.2 (std. dev. 15.2 | 55 | APACHE II 18.6 (std. dev. 9.7) | 32 | UK |
| | GSE10474 | Howrylak | Adults in MICU with sepsis +/− ALI | Admission to ICU | 34 | 57 (std. dev. 4.3) | 45 | APACHE II 20.7 (std. dev. 1.6) | 33 | USA |
| | GSE28658 | Khoo | Children with bacteremia | At diagnosis | 6 | 3.6 (std. dev. 2.2) | 33 | unk | unk | Nigeria |
| | GSE32707 | Dolinay | Adults in MICU with sepsis +/− ARDS | Admission to ICU | 48 | 57.1 (std. dev. 14.9) | 53 | APACHE II 26.7 (std. dev. 8.5) | 35 | USA |
| | GSE63042 | Langley | Adults with sepsis (CAPSOD study) | Admission to ED | 104 | 59.1 (std. dev. 18.3) | 59 | APACHE II 16.5 (std. dev. 7.3) | 37 | USA |
| | GSE63990 | Tsalik | Adults with bacterial infection plus 2+ SIRS criteria | Admission to ED | 70 | 49 (range 14-88) | 50 | unk. | 9 | USA |
| | GSE66890 | Kangelaris | Adults in ICU with sepsis +/− ARDS | Admission to ICU | 62 | 63 (std. dev 19) | 56 | APACHE III 100 (std. dev. 35) | 25 | USA |
| | GSE74224 | McHugh | Community-acquired sepsis with bacteremia | Within 24 hours of ICU admission | 74 | 62.5 | 55 | unk | unk | Australia & Netherlands |

Figure 4:
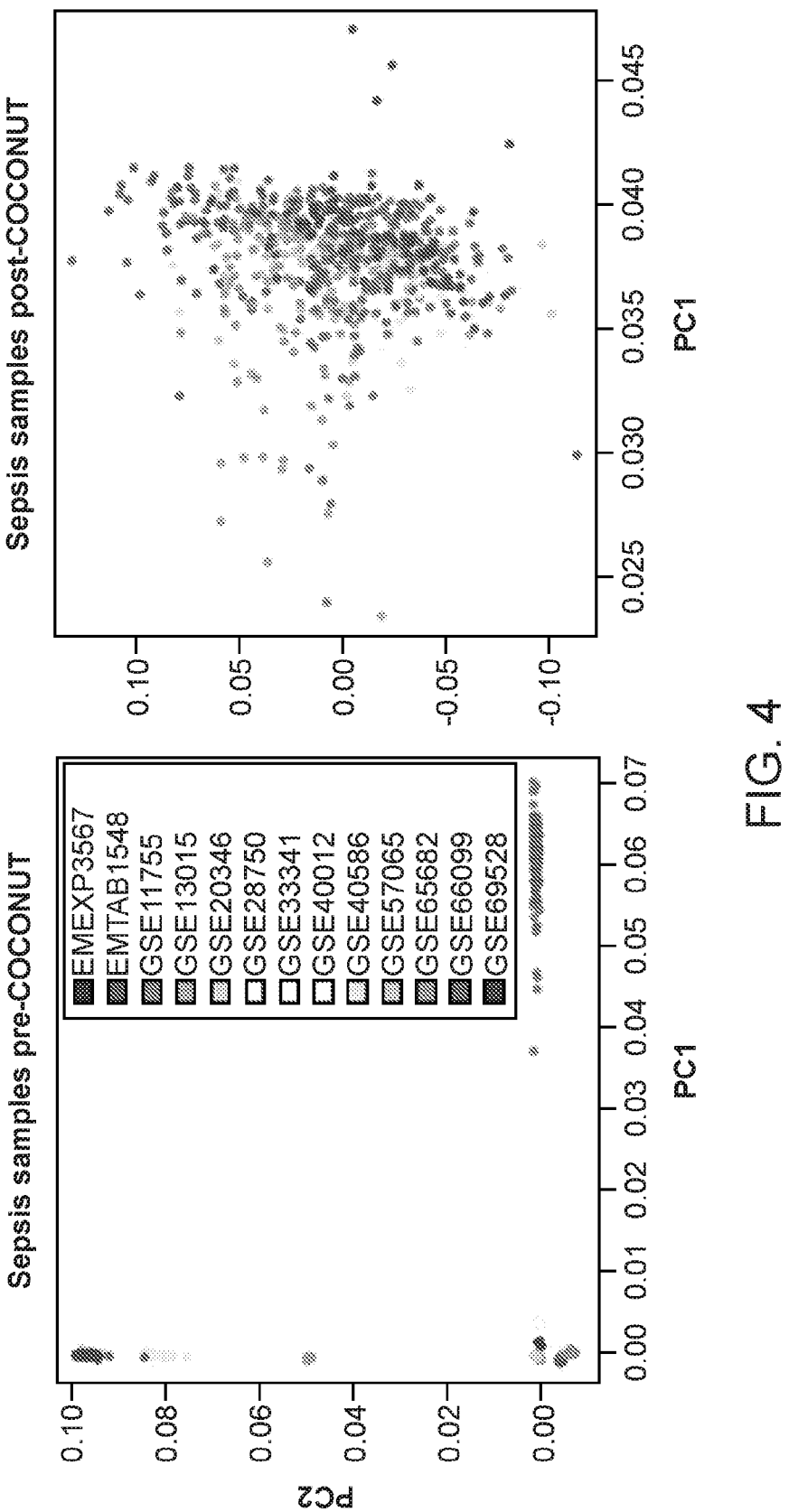
FIG. 4 depicts the principal components analysis of the discovery datasets pre- and post-COCONUT. Prior to COCONUT co-normalization, the discovery datasets are entirely separated by technical batch effects. These technical effects are removed post-COCONUT, as evidenced by a general overlapping of the discovery datasets in the first two principle components.
Figure 5:
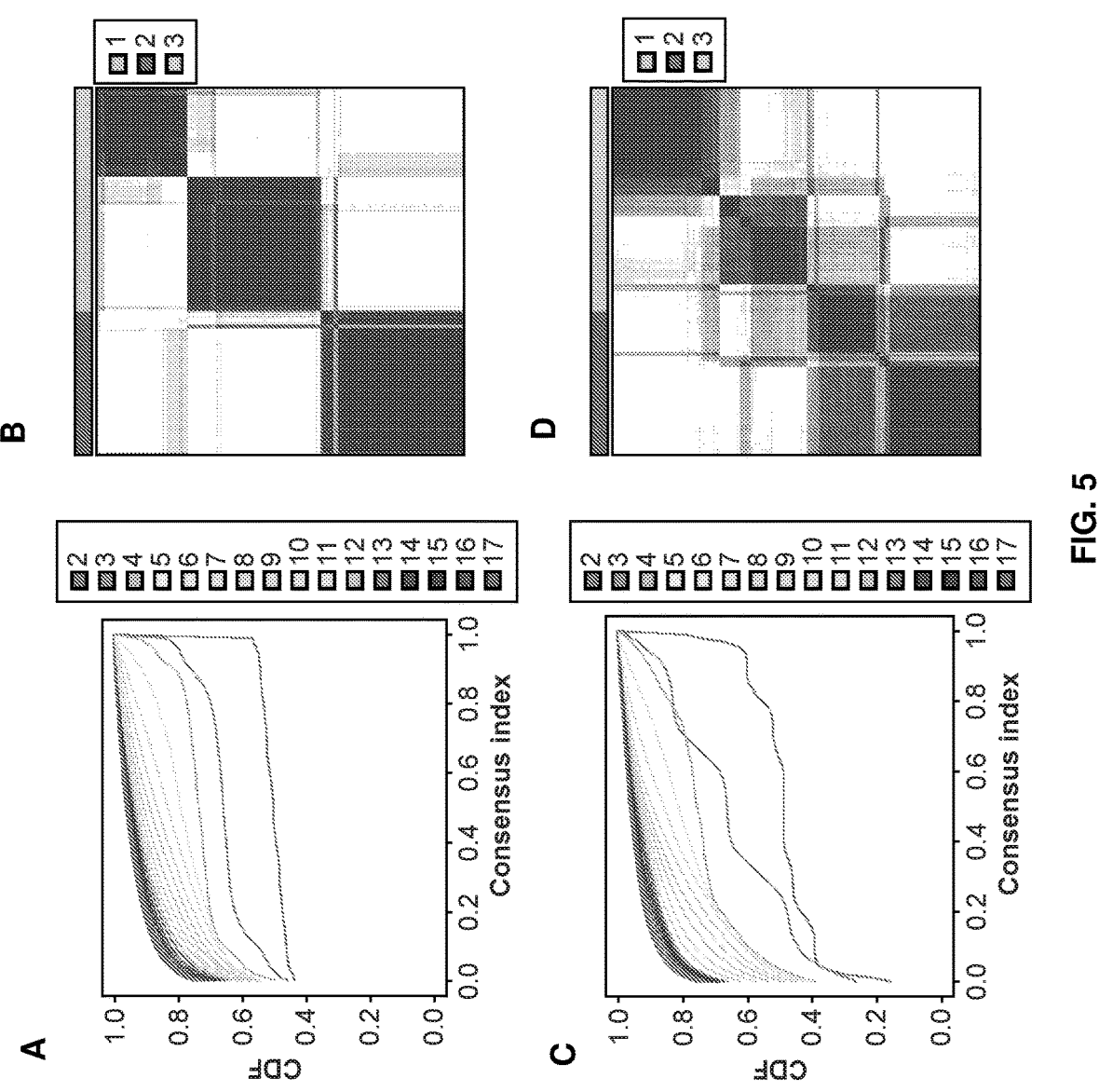
FIG. 5A-D depicts output from the two consensus clustering algorithms using K-means (A, B) and partitioning around medioids (C,D). (A,C) Cumulative density functions of consensus assignments by number of clusters. (B,D) Consensus mappings by cluster. 1=Inflammopathic, 2=Adaptive, 3=Coagulopathic.
Figure 6:
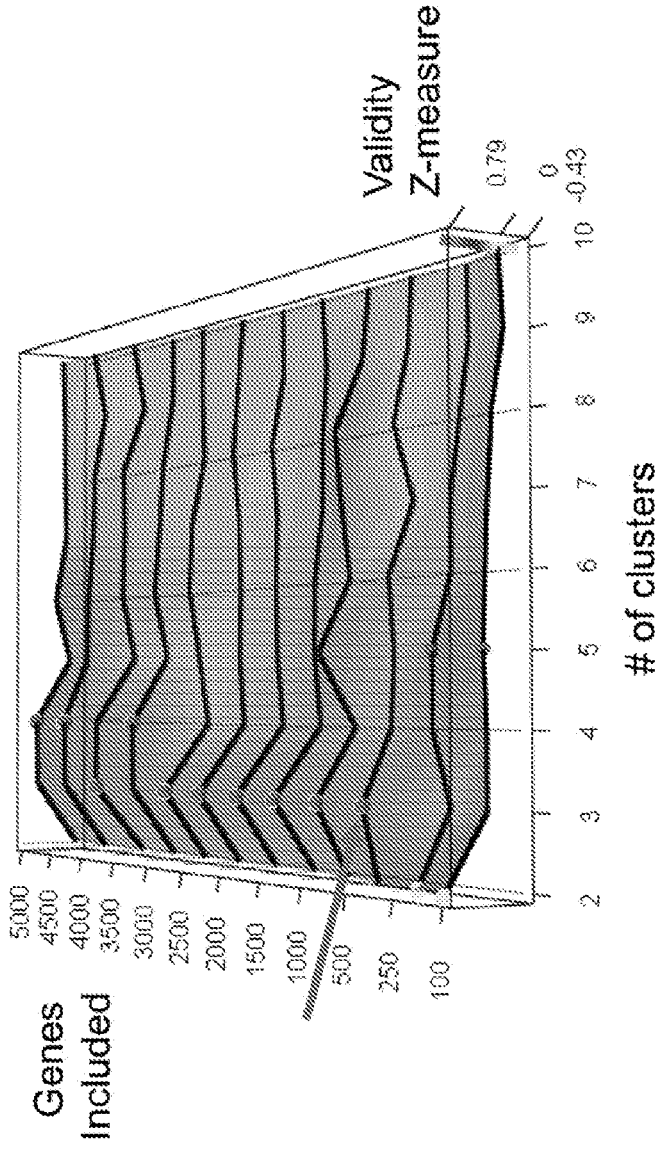
FIG. 6 depicts a COMMUNAL map of cluster optimality. X-axis shows number of clusters, Y-axis shows number of included genes, Z-axis shows mean validity score (higher is better). Red and blue dots show automatically assigned optima at each number of included genes. COMMUNAL automatically chose the following 5 validity measures: gap statistic, connectivity, average silhouette width, g3 metric, Pearson's gamma. The resulting map shows the mean of standardized values of each validity measure across the entire tested space. Stable optima at K=3 clusters are seen over most of the tested space, indicating strong, consistent

The 14 discovery datasets were first co-normalized into a single pooled cohort using the COCONUT method (15), providing batch-corrected, pooled sepsis data across a wide variety of clinical conditions (FIG. 4). There were 8,946 genes that were measured in all 14 pooled discovery datasets. The pooled data were then clustered using the COMMUNAL algorithm across 11 test points ranging from the top 100 to 5,000 genes using consensus K-means and consensus PAM clustering (individual clustering algorithm results shown in FIG. 5) (14). Visual inspection of the COMMUNAL optimality map showed clear, stable optima at K=3 clusters from 500 genes to 5,000 genes (FIG. 6). Further, the clustering at 500 genes was chosen as the optimal clustering assignment under the assumption that using the fewest number of genes had the least amount of noise or redundant signal. Based on gene ontology analysis described below, and to facilitate their easier understanding, the three clusters have been named "Inflammopathic", "Adaptive", and "Coagulopathic".

Figures 2A, 2B:
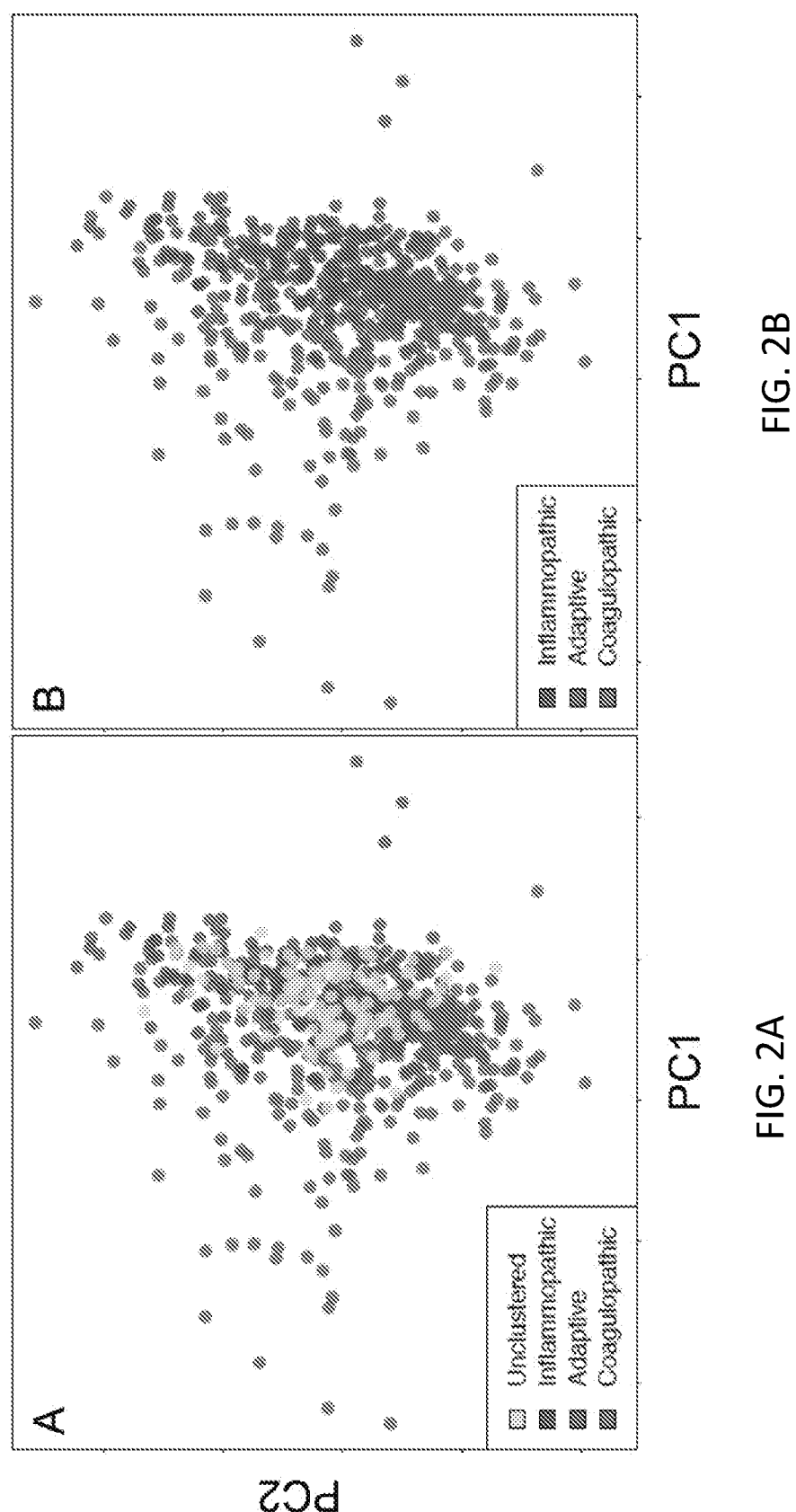
FIGS. 2A-2B depict the first two principal components (PCs) of the discovery clustering results (both with (A) and without (B) the 16% of samples that went unclustered in the final analysis, in gold) using all 8,946 genes present in the COCONUT conormalized data. Here it is shown that the cluster assignments that were recovered in an unsupervised manner are clearly separated in high-dimensional space, as demonstrated by the first two principal components.

To visualize their general separability, principal components analysis was performed on the discovery clusters using all genes both with and without the 'unclustered' sample (FIGS. 2A-2B). Details on the assignment of clusters in the Discovery datasets are available in the Supplemental Results, Table 12, and Supplemental FIGS. 4-5.

Gene Ontology Across the Different Clusters

To better understand the biology represented by the clusters, gene ontology over-representation analysis was used. Each of the 500 genes were assigned to one of the three discovery clusters based on absolute effect size (i.e., each gene was assigned to the cluster in which it was most different from the remaining two clusters). Each of the resulting three gene lists were tested for significance in gene ontology (GO) terms. The Inflammopathic cluster was significant for canonical pro-inflammatory signaling pathways such as IL-1 receptor, pattern recognition receptor activity, and complement activation. The Adaptive cluster was significant for several pathways related to adaptive immunity and interferon signaling. The third cluster was named Coagulopathic as it was significant for terms related to clotting and coagulation, such as platelet degranulation, glycosaminoglycan binding, and coagulation cascade.

Clinical Findings Across the Different Clusters

The differences between the discovery clusters in the demographic and clinical variables for which we had subject-level data (Table 2) were investigated.

TABLE 2

Demographic and clinical variables across discovery clusters. Not all variables were available
for all samples, so the totals are not always consistent; N for each measured variable is
included as a separate column. Statistics were calculated by pooling data among cohorts.

| Variable | Inflammopathic | Adaptive | Coagulopathic | P value (chisq/ ANOVA) | Total N used |
|---|---|---|---|---|---|
| Total Samples Assigned | 175 | 219 | 108 | | |
| Male (percent) | 58.4 | 59.4 | 61.5 | 0.864 | 481 |
| Age (years, +/−sd) | 34.8 (32.1) | 38.5 (28.7) | 49.7 (29.4) | 0.0001 | 452 |
| Age <18 (percent) | 16.8 | 17.6 | 15.9 | 0.930 | |
| Age >70 (percent) | 27.7 | 20.0 | 36.4 | 0.007 | |
| WBC count (+/−sd) | 18.02 (16.18) | 13.83 (10.64) | 12.87 (13.3) | 0.176 | 133 |
| Neutrophils (+/−sd) | 59.67 (18.31) | 61.14 (16.42) | 58.15 (23.1) | 0.843 | 107 |
| Bands (+/−sd) | 17.04 (12.77) | 11.58 (11.57) | 6.75 (6.13) | 0.002 | 107 |
| Lymphocytes (+/−sd) | 15.89 (13.8) | 20.17 (12.71) | 27.05 (23.16) | 0.024 | 107 |
| Monocytes (+/−sd) | 6.07 (4.33) | 6.19 (3.82) | 6.6 (6.66) | 0.91 | 107 |
| Immunosuppressed (percent) | 5.80 | 8.90 | 11.50 | 0.62 | 140 |
| Gram negative (percent) | 46.2 | 48.4 | 51.4 | 0.860 | 285 |
| Shock (percent) | 73.0 | 32.2 | 62.2 | 4.58E−10 | 297 |
| High Clinical Severity (percent) | 50.8 | 32.4 | 56.3 | 0.002 | 313 |
| Non-survivor (percent) | 29.8 | 8.1 | 25.4 | 8.01E−06 | 355 |

The following were found: significant differences in age (both the overall distribution, and the percent of patients >70 years of age), severity (as measured by percent of patients with clinical severity scores above the dataset mean, and/or in septic shock), and 30-day mortality. It was also found that the Inflammopathic cohort had greater bandemia and a lower lymphocyte percentage on white blood cell differential; however, differential was only available in a single cohort. This suggests that the Adaptive cluster is comprised of less sick patients with fewer elderly patients, while the Inflammopathic and Coagulopathic clusters separate the sicker patients into a younger and an older group. Addition of the 'unclustered' patients showed they have a balanced phenotype with respect to age and shock; their addition did not substantially change the demographic or clinical findings (Table 4). Since the unsupervised clustering did not take into account any clinical data whatsoever, finding a significant difference in mortality shows that the clusters represent distinct pathophysiological states of clinical relevance.

TABLE 4

Demographic and clinical variables according to discovery clusters, with unclustered samples
added as a group. Not all variables were available for all samples, so the totals are not
always consistent. Statistically significant differences between groups (age, shock, and
mortality) are the same as seen when unclustered samples are excluded (Table 2). However,
the addition of unclustered samples now results in a statistically significant difference
in frequency of Gram negative infections, which is higher in these subjects.

| | Inflammopathic | Adaptive | Coagulopathic | Unclustered | P value (chisq/ ANOVA) |
|---|---|---|---|---|---|
| Total Samples Assigned | 175 | 219 | 108 | 112 | |
| Male (percent) | 58.4 | 59.4 | 61.5 | 60.9 | 0.952 |
| (N, gender) | 166 | 180 | 135 | 92 | |
| Age (years, +/−sd) | 34.8 (32.1) | 38.5 (28.7) | 49.7 (29.4) | 45.1 (28.9) | 0.000152 |
| Age <18 years (percent) | 16.8 | 17.6 | 15.9 | 11.6 | 0.660 |
| Age >70 years (percent) | 27.7 | 20.0 | 36.4 | 24.4 | 0.01604 |
| (N, age) | 155 | 165 | 132 | 86 | |
| WBC count (+/−sd) | 18.02 (16.18) | 13.83 (10.64) | 12.87 (13.3) | 16.56 (10.36) | 0.29 |
| Neutrophils (+/−sd) | 59.67 (18.31) | 61.14 (16.42) | 58.15 (23.1) | 48.27 (19.4) | 0.15 |
| Bands (+/−sd) | 17.04 (12.77) | 11.58 (11.57) | 6.75 (6.13) | 15.87 (12.22) | 0.0048 |
| Lymphocytes (+/−sd) | 15.89 (13.8) | 20.17 (12.71) | 27.05 (23.16) | 29.87 (20.52) | 0.0068 |
| Monocytes (+/−sd) | 6.07 (4.33) | 6.19 (3.82) | 6.6 (6.66) | 4.33 (3.83) | 0.5 |
| (N, differential) | 55 | 36 | 21 | 15 | |
| Immunosuppressed (percent) | 5.8 | 8.9 | 11.5 | 10.5 | 0.78 |
| (N, immune status) | 69 | 45 | 26 | 19 | |
| Gram negative (percent) | 46.2 | 48.4 | 51.4 | 69.8 | 0.033 |
| (N, Gram status) | 91 | 157 | 37 | 53 | |
| Shock (percent) | 73.0 | 32.2 | 62.2 | 41.7 | 1.30E−09 |
| (N, shock status) | 100 | 152 | 45 | 48 | |
| High Clinical Severity (percent) | 50.8 | 32.4 | 56.3 | 50.0 | 0.005 |

TABLE 4-continued

Demographic and clinical variables according to discovery clusters, with unclustered samples added as a group. Not all variables were available for all samples, so the totals are not always consistent. Statistically significant differences between groups (age, shock, and mortality) are the same as seen when unclustered samples are excluded (Table 2). However, the addition of unclustered samples now results in a statistically significant difference in frequency of Gram negative infections, which is higher in these subjects.

| | Inflammopathic | Adaptive | Coagulopathic | Unclustered | P value (chisq/ ANOVA) |
|---|---|---|---|---|---|
| (N, clinical severity) | 124 | 102 | 87 | 68 | |
| 30-day mortality (percent) | 29.8 | 8.1 | 25.4 | 24.2 | 2.97E−05 |
| (N, survivor status) | 124 | 160 | 71 | 62 | |

Regression models were run on cluster membership (in a '1-vs-all' format) to assess the joint ability of age, shock, severity, and their interaction to predict cluster membership. In each case, the percent of variance explained by age, shock and severity was 9.7%, 6.4%, and 0.7% for the Inflammopathic, Adaptive, and Coagulopathic groups, respectively, in discovery (total N=251, Table 5). A sensitivity analysis showed that these results could only be explained away by an unmeasured confounding variable with a substantially greater effect size than the included variables (Table 5). Thus, while age, shock, and severity are significantly different across the groups, cluster assignment is much more complex than these three factors alone.

TABLE 5

Age, shock and severity as cluster predictors in discovery data. A. Multiple regression was run on each cluster type (vs. all others, plus unclustered) to determine whether age and shock (and their interaction) could predict cluster assignment. Shown are P-values for each covariate, along with final model $R^2$ values and unexplained residual variance. Only samples with sample-level age, shock, and severity data were used here. B. Risk ratios (RRs) for mortality by cluster, with resulting E-values. C. Age, shock and severity are shown to have lower RRs for mortality and for cluster assignment than the E-values in (B), showing that a confounding variable explaining the clusters would have to have a substantially greater effect size than age, shock, or severity. We can thus conclude that the observed risk ratios of mortality due to cluster assignment could be explained away by an unmeasured confounder that was associated with both cluster assignment and mortality by an effect size greater than 2.04-6.16 (depending on cluster), but that neither shock, high clinical severity, or age >70 years has an effect size of this magnitude.

| A | Inflammo- pathic | Adaptive | Coagulo- pathic | Unclustered |
|---|---|---|---|---|
| N with age & shock & severity data | 86 | 90 | 37 | 38 |
| intercept | 0.8274 | 0.0226 | 0.261 | 0.216 |
| age | 0.3437 | 0.4367 | 0.6 | 0.739 |
| shock | 0.2303 | 0.2529 | 0.731 | 0.713 |
| severity | 0.7622 | 0.9756 | 0.801 | 0.926 |
| age*shock | 0.0554 | 0.7794 | 0.178 | 0.469 |
| age*severity | 0.3202 | 0.2309 | 0.875 | 0.648 |
| shock*severity | 0.6119 | 0.5512 | 0.991 | 0.885 |
| age*shock*severity | 0.8052 | 0.4859 | 0.928 | 0.496 |
| Adjusted R-squared | 0.097 | 0.064 | 0.007 | −0.0001 |
| Percent of variance unexplained | 90.3 | 93.6 | 99.3 | 100 |

| B | RR mortality | E-value mortality |
|---|---|---|
| Inflammopathic | 1.90 | 3.21 |
| Adaptive | 0.30 | 6.16 |

TABLE 5-continued

Age, shock and severity as cluster predictors in discovery data. A. Multiple regression was run on each cluster type (vs. all others, plus unclustered) to determine whether age and shock (and their interaction) could predict cluster assignment. Shown are P-values for each covariate, along with final model $R^2$ values and unexplained residual variance. Only samples with sample-level age, shock, and severity data were used here. B. Risk ratios (RRs) for mortality by cluster, with resulting E-values. C. Age, shock and severity are shown to have lower RRs for mortality and for cluster assignment than the E-values in (B), showing that a confounding variable explaining the clusters would have to have a substantially greater effect size than age, shock, or severity. We can thus conclude that the observed risk ratios of mortality due to cluster assignment could be explained away by an unmeasured confounder that was associated with both cluster assignment and mortality by an effect size greater than 2.04-6.16 (depending on cluster), but that neither shock, high clinical severity, or age >70 years has an effect size of this magnitude.

| Coagulopathic | 1.35 | | 2.04 |
|---|---|---|---|

| C | RR mortality | RR Inflammopathic | RR Adaptive | RR Coagulopathic |
|---|---|---|---|---|
| Shock | 0.97 | 2.78 | 0.49 | 1.70 |
| High severity | 1.49 | 1.17 | 0.54 | 1.46 |
| Age >70 years | 1.26 | 1.04 | 0.68 | 155.5 |

Validation of Cluster Classifier in Independent Datasets

Having characterized the sepsis clusters in the discovery datasets, it was hypothesized that these same clusters could be recovered in independent validation datasets using a discrete classifier. A gene-expression-based classifier for cluster assignment was built so that the cluster hypothesis could be tested and applied in external validation datasets. Briefly, the classifier assigns each sample three scores (one for each cluster type) and then applies multiclass regression to output a final cluster assignment (Table 6A-B). The classifier used a total of 33 genes, and yielded an overall 83% accuracy in leave-one-out re-assignment of the samples on which it was trained (Table 6C). The greatest classifier inaccuracy is in distinguishing Inflammopathic patients from Coagulopathic patients (FIG. 9). The classifier was applied to the 9 bacterial sepsis validation datasets (Table 7)(12, 38-44), and judged the classifier's accuracy by its ability to recover clusters with similar molecular and clinical phenotypes to the discovery clusters. Since the 9 validation datasets are independent from one another, the same demographic and clinical variables as in the discovery clusters were examined in both a pooled fashion (Table 3) and treating each dataset independently (Table 8). As the individual datasets may be underpowered to detect differences, statistical tests were run in the pooled data; compared to the discovery clusters, the same patterns of significance were observed. The Coagulopathic cluster had significantly more patients older than 70 years (P<0.05), whereas the Adaptive cluster had fewer patients with shock (P<0.01), fewer patients with high clinical severity (P<0.05) and a lower mortality (P=0.01).

TABLE 3

Demographic and clinical variables across validation clusters. Not all variables were available for all samples, so the totals are not always consistent. N for each measured variable is included as a separate row. Statistics are shown both by aggregating cohort-level statistics, and by pooling data among cohorts.

| Variable | Inflammopathic | Adaptive | Coagulopathic | P value (chisq/ ANOVA) | Total N used | Number of Datasets |
|---|---|---|---|---|---|---|
| Total Samples Assigned | 208 | 264 | 128 | | 600 | 9 |
| Male (pooled percent) | 51.7 | 62.5 | 60.0 | 0.08153 | 519 | 7 |
| Age (pooled mean, sd) | 57.9 (20.9) | 57.3 (19.7) | 60.9 (23.1) | 0.3210 | 520 | 7 |
| Age >70 Y (pooled percent) | 32.2 | 28.0 | 43.5 | 0.016 | 520 | 7 |
| WBC count (+/−sd) | 18.48 (11.12) | 16.94 (21.61) | 14.57 (7.79) | 0.67 | 104 | 1 |
| Neutrophils (+/−sd) | 81.27 (17.33) | 76.8 (17.51) | 84.19 (11.72) | 0.22 | 93 | 1 |
| Bands (+/−sd) | 12.82 (17.81) | 2.5 (6.62) | 5.83 (9.07) | 0.035 | 51 | 1 |
| Lymphocytes (+/−sd) | 6.96 (4.76) | 11.84 (8.46) | 5.95 (4.94) | 0.001 | 93 | 1 |
| Monocytes (+/−sd) | 4.24 (2.82) | 6.85 (4.44) | 5.03 (3.19) | 0.01 | 93 | 1 |
| Immunosuppressed (percent) | 2.9 | 6.4 | 13 | 0.32 | 104 | 1 |
| Gram negative (pooled percent) | 66.7 | 78.3 | 61.1 | 0.468 | 68 | 3 |
| Shock (pooled percent) | 69.8 | 36.7 | 45.5 | 0.0036 | 136 | 2 |
| High Clinical Severity (pooled percent) | 45.5 | 31.8 | 39.6 | 0.030 | 450 | 6 |
| Non-survivor (pooled percent) | 29.3 | 18.5 | 31.1 | 0.01095 | 514 | 7 |

TABLE 6

The classifier for cluster assignments. (A) Genes that make up the three subparts of the classifier score. (B) Coefficients for regression classifier; each 'score' refers to the geometric mean difference of 'Up' minus 'Down' genes for each class defined in (A). The scores are multiplied through the given regression coefficients to form final predicted probabilities of cluster assignment. (C) Two-way matrix for re-assignment of discovery clusters comparing "True" assignment from the original COMMUNAL clustering to predicted assignment by the cluster classifier.

A

| | Inflammopathic | | Adaptive | | Coagulopathic | |
|---|---|---|---|---|---|---|
| Up | Down | Up | Down | Up | Down |
| ARG1 | HLA-DMB | YKT6 | GADD45A | KCNMB4 | RHBDF2 |
| LCN2 | | PDE4B | CD24 | CRISP2 | ZCCHC4 |
| LTF | | TWISTNB | S100A12 | HTRA1 | YKT6 |
| OLFM4 | | BTN2A2 | STX1A | PPL | DDX6 |
| | | ZBTB33 | | | SENP5 |
| | | PSMB9 | | | RAPGEF1 |
| | | CAMK4 | | | DTX2 |
| | | TMEM19 | | | RELB |
| | | SLC12A7 | | | |
| | | TP53BP1 | | | |
| | | PLEKHO1 | | | |
| | | SLC25A22 | | | |
| | | FRS2 | | | |

TABLE 6-continued

The classifier for cluster assignments. (A) Genes that make up the three subparts
of the classifier score. (B) Coefficients for regression classifier; each
'score' refers to the geometric mean difference of 'Up' minus
'Down' genes for each class defined in (A). The scores are multiplied
through the given regression coefficients to form final predicted probabilities
of cluster assignment. (C) Two-way matrix for re-assignment of discovery
clusters comparing "True" assignment from the original COMMUNAL clustering
to predicted assignment by the cluster classifier.

| B | Intercept | Inflammopathic Score | Adaptive Score | Coagulopathic Score |
|---|---|---|---|---|
| Adaptive | −0.617 | −3.150 | 7.187 | 1.594 |
| Coagulopathic | 0.494 | −1.382 | 0.480 | 1.569 |

| | | True | | |
|---|---|---|---|---|
| C | | Inflammopathic | Adaptive | Coagulopathic |
| Predicted | Inflammopathic | 156 | 4 | 41 |
| | Adaptive | 4 | 236 | 13 |
| | Coagulopathic | 30 | 7 | 97 |

TABLE 7

Breakdown of cluster assignments in the validation cohorts.
Each subject was assigned to the most likely sepsis
cluster based on the 33-gene cluster classifier.

| | Inflammopathic | Adaptive | Coagulopathic |
|---|---|---|---|
| EMEXP3850 | 9 | 8 | 7 |
| EMTAB4421.51 | 63 | 78 | 37 |
| GSE10474 | 14 | 14 | 6 |
| GSE28658 | 2 | 3 | 1 |
| GSE32707 | 18 | 21 | 9 |

TABLE 7-continued

Breakdown of cluster assignments in the validation cohorts.
Each subject was assigned to the most likely sepsis
cluster based on the 33-gene cluster classifier.

| | Inflammopathic | Adaptive | Coagulopathic |
|---|---|---|---|
| GSE63042 | 34 | 47 | 23 |
| GSE63990 | 25 | 33 | 12 |
| GSE66890 | 18 | 30 | 14 |
| GSE74224 | 25 | 30 | 19 |

TABLE 8

Demographic and outcomes data shown per cluster per validation dataset. Not all
variables were available for all datasets, so each variable is shown only for
the datasets that included the given variable. Note that no 'unclustered'
samples are present because the classifier does not output an 'unclustered' class.

| | Inflammopathic | Adaptive | Coagulopathic | Dataset N |
|---|---|---|---|---|
| Male, Percent | | | | |
| EMEXP3850 | 11.1% | 62.5% | 42.9% | 24 |
| EMTAB4421.51 | 57.1% | 75.6% | 59.5% | 178 |
| GSE10474 | 35.7% | 61.5% | 66.7% | 34 |
| GSE32707 | 33.3% | 57.1% | 44.4% | 48 |
| GSE63042 | 67.6% | 57.4% | 52.2% | 104 |
| GSE66890 | 55.6% | 53.3% | 64.3% | 62 |
| GSE74224 | 50.0% | 46.4% | 78.9% | 74 |
| mean (sd) | 44.4 (17.6) | 59.1 (8.4) | 58.4 (12.0) | |
| Age, mean (years) | | | | |
| EMEXP3850 | 1.574 | 0.8438 | 1.369 | 24 |
| EMTAB4421.51 | 59.59 | 66.23 | 66.7 | 178 |
| GSE10474 | 65.36 | 48.92 | 60.5 | 33 |
| GSE32707 | 59.06 | 54.33 | 59.78 | 48 |
| GSE63042 | 62.94 | 53.87 | 63.13 | 104 |
| GSE66890 | 61 | 59.03 | 73.21 | 62 |
| GSE74224 | 59.5 | 59 | 60.21 | 74 |
| mean (sd) | 52.7 (14.7) | 48.8 (13.6) | 55.0 (15.2) | |
| Gram Negative, Percent | | | | |
| EMEXP3850 | 100.0% | 100.0% | 100.0% | 24 |
| GSE28658 | 100.0% | 100.0% | 100.0% | 6 |
| GSE74224 | 43.8% | 58.3% | 30.0% | 74 |
| mean (sd) | 81.2 (25.5) | 86.1 (19.6) | 76.6 (33.0) | |

TABLE 8-continued

Demographic and outcomes data shown per cluster per validation dataset. Not all
variables were available for all datasets, so each variable is shown only for
the datasets that included the given variable. Note that no 'unclustered'
samples are present because the classifier does not output an 'unclustered' class.

|  | Inflammopathic | Adaptive | Coagulopathic | Dataset N |
|---|---|---|---|---|
| Septic Shock, Percent | | | | |
| GSE66890 | 83.3% | 43.3% | 42.9% | 62 |
| GSE74224 | 60.0% | 30.0% | 47.4% | 74 |
| mean (sd) | 71.7 (11.7) | 36.7 (6.7) | 45.1 (0.0) | |
| High Clinical Severity, Percent | | | | |
| EMEXP3850 | 77.8% | 25.0% | 28.6% | 24 |
| EMTAB4421.51 | 44.4% | 26.9% | 29.7% | 178 |
| GSE10474 | 42.9% | 35.7% | 50.0% | 33 |
| GSE32707 | 44.4% | 38.1% | 66.7% | 48 |
| GSE63042 | 47.1% | 17.0% | 52.2% | 104 |
| GSE66890 | 33.3% | 63.3% | 28.6% | 62 |
| mean (sd) | 48.3 (13.8) | 34.3 (14.7) | 42.6 (14.6) | |
| Mortality | | | | |
| EMEXP3850 | 22.2% | 25.0% | 14.3% | 24 |
| EMTAB4421.51 | 33.3% | 21.8% | 24.3% | 178 |
| GSE10474 | 28.6% | 38.5% | 33.3% | 33 |
| GSE32707 | 38.9% | 28.6% | 44.4% | 48 |
| GSE63042 | 29.4% | 17.0% | 43.5% | 104 |
| GSE63990 | 8.0% | 6.1% | 16.7% | 70 |
| GSE66890 | 38.9% | 7.4% | 41.7% | 62 |
| mean (sd) | 28.5 (10.0) | 20.6 (10.7) | 31.2 (11.9) | |

The Coagulopathic cluster also was associated with clinical coagulopathy, including disseminated intravascular coagulation ($P<0.05$, Tables 9-10 and Supplemental Results).

TABLE 9

Association of clinical coagulopathy with the Coagulopathic cluster.
(A) GSE66099 (Discovery dataset, pediatric), disseminated intravascular
coagulation (DIC) by cluster type. (B) GSE63042 (Validation
dataset, adults) intersection of thrombocytopenia (platelets
<100,000) and prolonged INR (>1.3) by cluster type. Association
p-value tested with Fisher Exact test.

| | GSE66099, Discovery: DIC | | | |
|---|---|---|---|---|
| A | No | Yes | Percent Yes | P Value |
| Inflammopathic | 64 | 12 | 15.8 | 0.0078 |
| Adaptive | 53 | 5 | 8.6 | |
| Coagulopathic | 20 | 11 | 35.5 | |
| Unclustered | 18 | 5 | 21.7 | |

| | GSE63042 (Validation): Platelet count <100,000 & INR >1.3 | | | |
|---|---|---|---|---|
| B | No | Yes | Percent Yes | P Value |
| Inflammopathic | 29 | 2 | 6.5 | 0.034 |
| Adaptive | 37 | 2 | 5.1 | |
| Coagulopathic | 16 | 6 | 27.3 | |

TABLE 10

Neither thrombocytopenia nor prolonged INR were significantly
associated with cluster type, though INR >1.3 showed
a trend towards significance in the Coagulopathic group.
Association p-value tested with Fisher Exact test.

| | | platelet count <100K | | | |
|---|---|---|---|---|---|
| A | | No | Yes | Percent Yes | P Value |
| GSE63042 | Inflammopathic | 27 | 6 | 18 | 0.3352 |
| (Validation) | Adaptive | 35 | 5 | 13 | |
| | Coagulopathic | 16 | 6 | 27 | |

| | | INR >1.3 | | | |
|---|---|---|---|---|---|
| B | | No | Yes | Percent Yes | P Value |
| GSE63042 | Inflammopathic | 10 | 13 | 57 | 0.0873 |
| (Validation) | Adaptive | 10 | 11 | 52 | |
| | Coagulopathic | 1 | 10 | 91 | |

TABLE 11

Comparison of cluster assignments to previously published clusters
from (A) Wong et al. and (B) Davenport et al. Goodman and Kruskal's
lambda for dependence was performed in both directions. Non-overlap
of the 95% CI with 0 is considered significant.

| | | Wong Endotypes | |
|---|---|---|---|
| | A | A | B |
| Clusters | Inflammopathic | 9 | 60 |
| | Adaptive | 23 | 22 |
| | Coagulopathic | 13 | 13 |
| | Unclustered | 7 | 12 |

TABLE 11-continued

Comparison of cluster assignments to previously published clusters
from (A) Wong et al. and (B) Davenport et al. Goodman and Kruskal's
lambda for dependence was performed in both directions. Non-overlap
of the 95% CI with 0 is considered significant.

Excluding 'unclustered': Lambda, (Wong|Core): 0.19, 95% CI 0.06-0.33
Including 'unclustered': Lambda, (Wong|Core): 0.15, 95% CI 0.04-0.27
Excluding 'unclustered': Lambda, (Core|Wong): 0.02, 95% CI 0-0.38
Including 'unclustered': Lambda, (Core|Wong): 0.02, 95% CI 0-0.33

| | | Davenport SRS Groups | |
| --- | --- | --- | --- |
| | B | 1 | 2 |
| Clusters | Inflammopathic | 61 | 2 |
| | Adaptive | 12 | 65 |
| | Coagulopathic | 20 | 17 |
| Lambda, (Davenport|Core): 0.49, 95% CI 0.37-0.61 | | | |
| Lambda, (Core|Davenport): 0.63, 95% CI 0.51-0.76 | | | |

Molecular Similarity Between Clusters Identified in Discovery and Validation

Figure 3A:
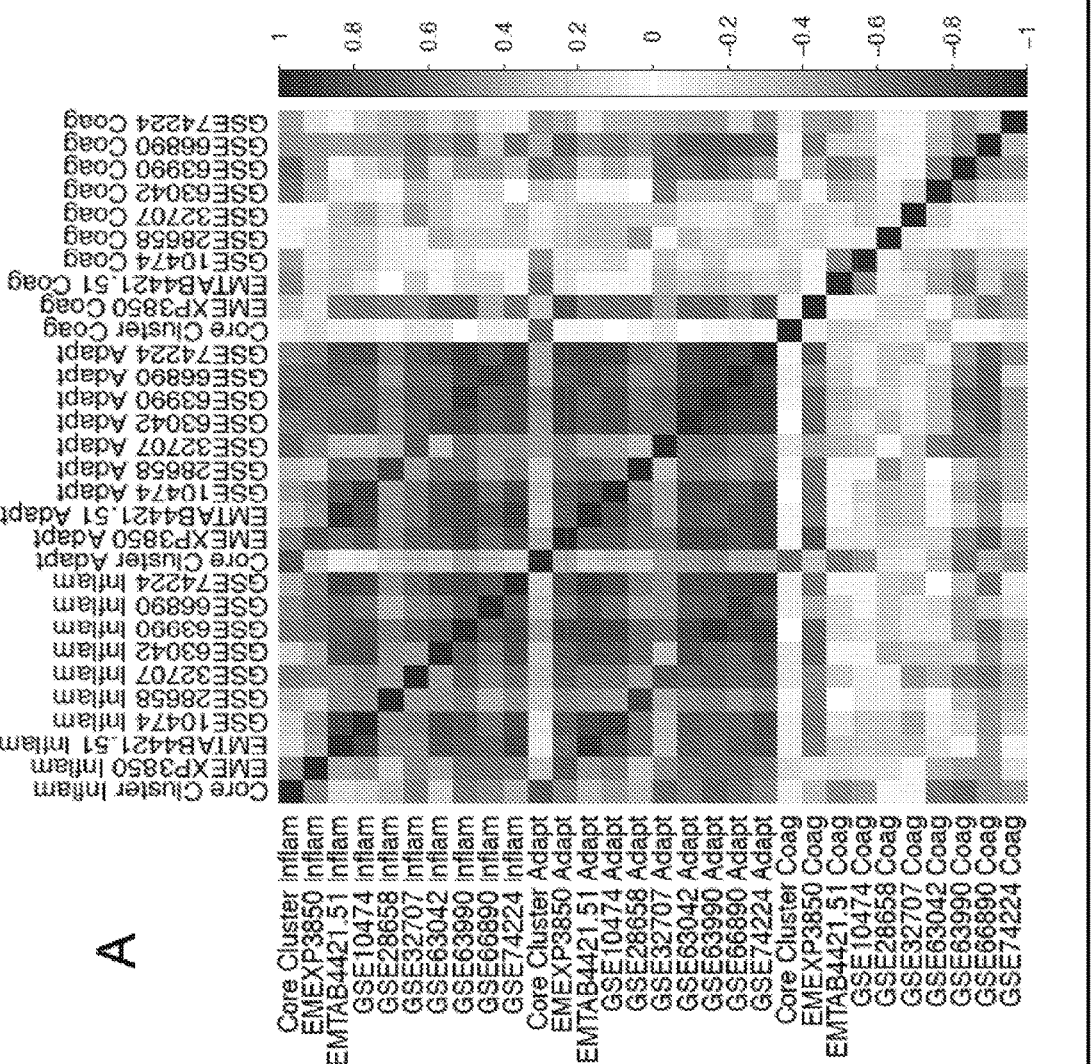
FIGS. 3A-3B depict correlations of average 500-gene expression vectors between clusters assigned in the discovery and validation datasets and a heatmap of Gene Ontology (GO) codes found to be overrepresented in the different clusters. (A) Correlations of average 500-gene expression vectors between clusters assigned in the discovery and validation datasets; correlation coefficient is shown by color (legend at figure right). Notably, samples from Inflammopathic clusters are positively correlated with Inflammopathic samples from other datasets, and negatively correlated with Adaptive samples from other datasets (and vice-versa). The Coagulopathic clusters show less cohesion but are positively correlated with one another. (B) Heatmap of Gene Ontology (GO) codes found to be overrepresented in the different clusters, colored by significance levels. In both (A) and (B), the pooled 'Core' discovery datasets are represented by a single column for each cluster, while each cluster in each validation dataset is represented by a separate column. Both sub-figures show a block structure indicative of molecular similarity across datasets between clusters of the same type.

Since the validation clusters were assigned with information from only 33 genes, it was investigated whether similar biology was present in the full gene expression profiles across discovery and validation clusters. First, the mean gene expression profiles for all 500 clustering genes were calculated, and correlation between the clusters was tested. Significant correlation would indicate that the classifier was capturing most of the information from the original clustering; the 33 genes used in the classifier were thus excluded from this analysis to avoid bias. Pearson correlations in mean gene expression profiles within the assigned clusters were high (Inflammopathic cluster, 0.59±0.18; Adaptive cluster, 0.67±0.19; Coagulopathic cluster, 0.20±0.21, FIG. 3A). These correlations were significant (P<0.01) between the discovery and validation clusters for all datasets for Inflammopathic, all datasets for Adaptive, and five out of nine datasets for Coagulopathic. As a comparison, 1000 random samples of 500 genes yielded mean correlations of 0.01-0.02.

Figure 3B:
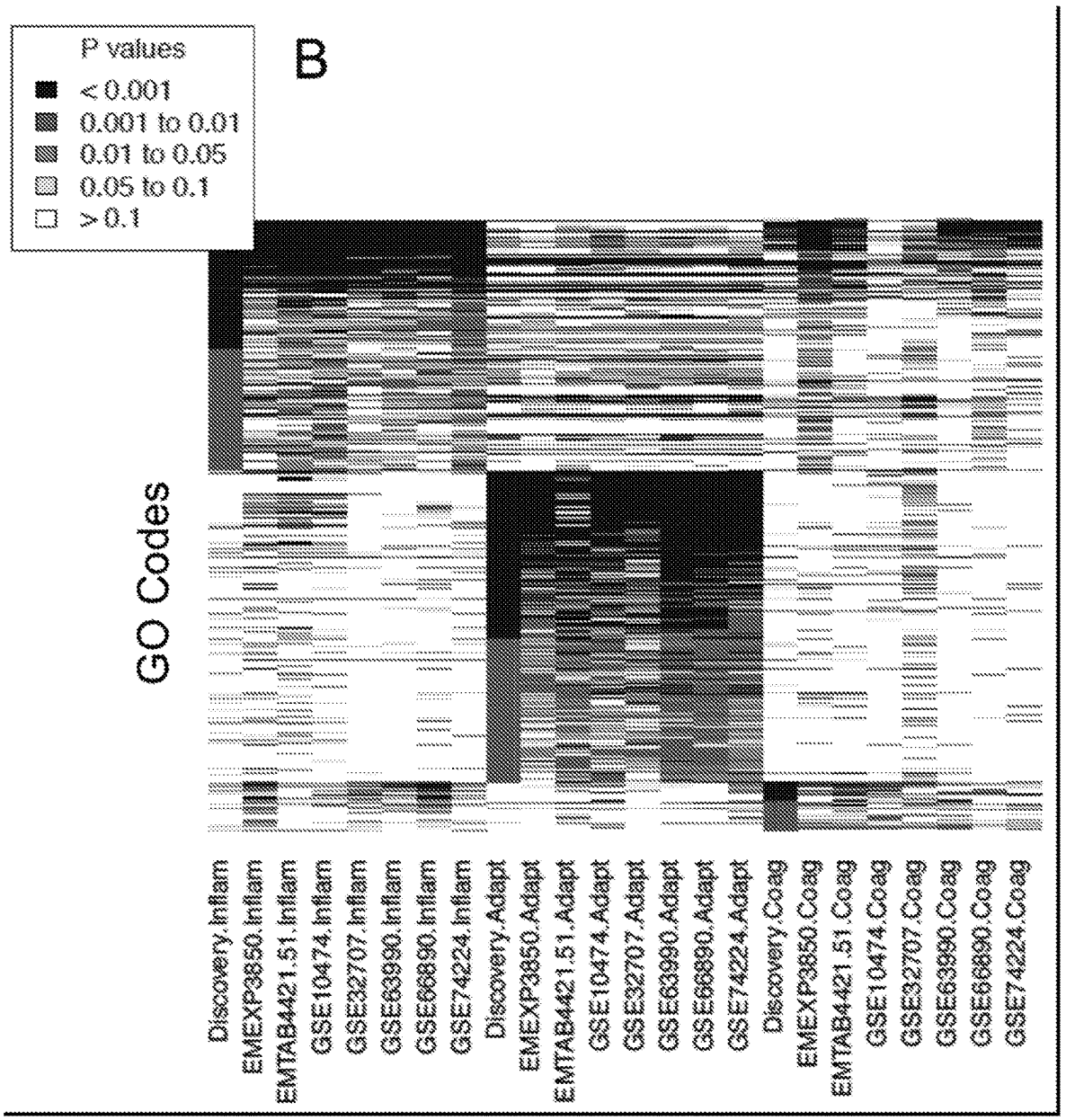

Next, it was tested whether the same Gene Ontology (GO) codes were overrepresented between validation clusters, as compared to the discovery clusters (FIG. 3B). On average, 68%, 87%, and 61% of the codes found significant at p<0.01 in the discovery clusters (Inflammopathic, Adaptive, and Coagulopathic, respectively) were identified as significant at p<0.05 in the same clusters in validation. In addition, a block structure is seen within clusters of the same type, indicating generally shared pathway enrichment within cluster types.

Comparison to Previously Established Sepsis Endotypes

Two groups have previously performed clustering using sepsis transcriptomic profiles. Wong et al. (9-11) and Davenport et al. (12, 13). The present cluster assignments were compared to the previously published assignments and showed significant overlaps with the Inflammopathic and Adaptive clusters (Supplemental Results and Table 10).

Discussion

The present study performed an unsupervised clustering analysis on pooled transcriptomic profiles (N=700) from 14 datasets from a broad range of subjects with bacterial sepsis, demonstrating that there are three robust sepsis clusters (or 'endotypes'). These clusters have been named Inflammopathic (higher mortality, innate immune activation), Adaptive (lower mortality, adaptive immune activation), and Coagulopathic (higher mortality, older, and with clinical and molecular evidence of coagulopathy), based on their molecular and clinical profiles. Next, it was shown that a 33-gene classifier that assigns subjects to these three clusters is able to recover the clinical and molecular phenotypes in 9 independent validation datasets (N=600). Finally, it was shown that these clusters can significantly explain the clusters derived by independent groups using different methods (9, 12). Taken together, these results demonstrate that the host response in the sepsis syndrome can be broadly defined by these three robust clusters.

Notably, each of the validation datasets had separate inclusion/exclusion criteria, providing a sort of sensitivity analysis that the identified clusters appear in both pooled settings (as in discovery) but also in more uniform, carefully phenotyped cohorts. For instance, samples from pediatric and adult datasets in discovery were pooled, but the methods did not simply cluster patients by age; then in validation, two datasets were pediatric and seven were adult, but all datasets contained a mix of all three sepsis clusters. The fact that the same broad phenotypic and molecular differences in these independent applications of the cluster classifier was redemonstrated is strong evidence that cluster membership is present across populations.

Despite the outcome differences across the three clusters, their clinical utility is not merely the ability to risk-stratify in terms of mortality. Mortality prediction is better achieved through purpose-built classifiers, which have been demonstrated with these same data(18). Instead, the hypothesis that underlies the search for sepsis clusters is that 'sepsis' represents multiple different disease states and manifests in many different ways (3, 6, 45). The aim of the present study was thus to uncover these subclinical clusters using a very large pool of sepsis patients across a wide range of clinical conditions. Uncovering and defining this heterogeneity allows for greater success in the discovery and validation of therapies that are beneficial only to one sepsis cluster, but may be neutral or even harmful to other clusters(11). For instance, both the molecular and clinical data suggest that the Coagulopathic cluster is associated with functional coagulopathy. Given the association of sepsis with clinical coagulopathies, and despite (or perhaps because of) the failure of most therapeutic interventions for coagulopathy in sepsis (3, 46, 47), further study of the Coagulopathic cluster is warranted. Similarly, drugs being tested in sepsis that are known to modulate the innate or adaptive immune systems (such as anti-IL-1 or anti-PD-L1 treatments (48, 49)) should find efficacy in the Inflammopathic or Adaptive clusters, respectively.

Pathobiology for the clusters was inferred by assigning each gene to the cluster in which it showed the greatest differential change from the other clusters. For instance, the association of innate immune pathways in the Inflammopathic cluster is indicative not of 'normal' innate immune activation, but rather of overactivation of the innate immune system, or of a relative lack of activation of adaptive immune genes, in Inflammopathic patients as compared to other septic patients. Similarly, the relatively higher adaptive immune gene activation in the Adaptive cluster is linked to its lower mortality. Seen through this lens, the three sepsis clusters show biological insights that, to some degree, reflect clinical intuitions. The early overactivation of the innate immune system or coagulation cascade in sepsis is linked to higher mortality, while the relative lack of these changes and the expansion of the adaptive immune response is linked to better outcome(50). Furthermore, since genes were selected based on absolute effect size, similarity in gene ontology pathway analysis between Inflammopathic and Adaptive clusters could be reflective of opposite modulation of similar pathways; this is further suggested by the strong inverse correlation between the Inflammopathic and Adaptive clusters in FIGS. 2A-2B. As above, these biological insights can be used to guide treatments for different subtypes.

Two independent research groups have identified sepsis subgroups: one focused on pediatric sepsis in a US-based cohort (9, 10); the other focused on adult sepsis in UK-based cohorts (12, 13). Notably, the two subgroupings do not broadly overlap. Comparison of the three clusters with the prior clusterings yielded several interesting findings. First, using subject-level comparisons, patients assigned to the Inflammopathic cluster were mostly assigned to Endotype B (11) or SRS 1 (12). However, Endotype B conferred a lower mortality in children compared to Endotype A, while SRS 1 conferred a higher mortality in adults compared to SRS2. Still, it was reassuring that these independent studies identified the same grouping of patients using completely separate techniques. Similarly, patients assigned to the Adaptive cluster were primarily assigned to SRS 2; both studies identified this as a low mortality group associated with interferon signaling. A third (Coagulopathic) cluster was also identified. The substantially larger sample size and greater heterogeneity of the discovery cohorts compared to prior work allowed the detection of this third Coagulopathic cluster.

Supplemental Methods

The COMMUNAL Algorithm

A common clustering approach would apply a single clustering algorithm (e.g., k-means clustering) and a single validation metric (e.g., the gap statistic (1)) at a single number of variables (e.g., 1,000 genes, usually chosen arbitrarily) to determine clusters. However, this approach can lead to unstable, non-reproducible results (2). Here the present study used the COmbined Mapping of Multiple clUsteriNg ALgorithms (COMMUNAL) method, which integrates data from multiple clustering algorithms and validity metrics across a range of included variables to identify the most robust number of clusters present in the data (2).

In unsupervised clustering, high-dimensional distance calculations between samples are used to identify subgroupings in the data. It is thus important to include variables (here, genes) that are likely to be informative while minimizing non-informative variables, so as to increase the signal-to-noise ratio. In a typical single-dataset clustering algorithm, usually some measure of variance is used to rank variables. Across multiple co-clustered datasets, however, the potential for high variance due to inter-dataset technical differences means that this metric may be less useful. The top 5,000 genes across the discovery datasets were ranked using an algorithm that accounts for both within-dataset variance and between-dataset variance (measured via mean absolute deviance)(3). The algorithm works as follows: median absolute deviation (MAD) is first used to rank all genes within each dataset, such that genes with the largest MAD are ranked highest. The median overall ranking is calculated across datasets. However, since the distribution of clusters may be different in each dataset, this meta-ranking may down-weight informative genes from unevenly distributed datasets. Thus, the top 20 genes from each individual dataset are also included (this number is arbitrary but set as default by the original algorithm authors). A final meta-ranking algorithm incorporates the top individual and pooled gene rankings into a single list. Further details can be found in the original manuscript by Planey & Gevaert (Genome Med, 2016), and in the accompanying software package 'Coincide' (https://github.com/kplaney/CoINcIDE). These ranked genes were then progressively included in the COMMUNAL algorithm.

Gene Ontology Testing

To validate whether the different clusters were indicative of different biology, each of the genes used in the final clustering was assigned to the cluster in which the gene had the highest absolute effect size using the Significance Analysis for Microarrays (SAM) method (4). Since these genes had a generally high variance across samples, higher differential expression of a gene within a given cluster suggests it contributes to that cluster's identity. Gene ontology (GO) enrichment was performed using ToppGene for the resulting gene lists (5). A Benjamini-Hochberg corrected p-value smaller than 0.05 was used as the significance threshold.

Cluster Classifier and Application in Validation Datasets

External validation is a key component of any exercise in clustering. However, in validation, it is important to switch to a supervised method (classification) rather than continuing to simply used unsupervised clustering in new validation datasets. There are two primary reasons for this. First, a de novo clustering does not produce labels. If a clustering was run on each new dataset, and it produced 3 clusters (call them A, B, C), there would be no way of matching the new clusters to the discovery (Inflammopathic/Coagulopathic/Adaptive) clusters. Instead, it would be necessary to rely on trying to 'pattern match' the closest phenotypic and molecular profiles (e.g. C=Inflammopathic, A=Coagulopathic, B=Adaptive) but this clearly introduces a large bias. The classifier, on the other hand, directly produces a label; thus it can be directly asked whether a validation sample classified as 'Inflammopathic' matches the discovery 'Inflammopathic' phenotypic and molecular profile, which is a more relevant clinical question. The second reason to derive a classifier is that without one, there is no way to assign a single new patient to a sample in a clinical setting. This is because clustering relies on the presence of an entire cohort to establish relative distances between samples, and so can only be done retrospectively. In contrast, classification can determine a subtype assignment for a single patient prospectively. If, for instance, it was necessary to identify to which cluster a patient belongs when he or she were admitted to hospital, a validated classifier would be necessary.

Thus, a gene-expression-based classifier for the resulting clusters was built using a two-step process in a 1-vs.-all, round-robin fashion for all clusters using all genes. First, SAM examining all genes (not just the genes used in clustering) was used to find genes statistically significantly associate with a given cluster. A greedy forward search was used to find a gene set that maximally separated the given cluster from all other clusters (6). If there are K clusters, such a method would produce K scores; thus, a multiclass logistic regression model was fit to the K scores as the final classifier using the R package nnet. Thus, to apply the classifier to an external dataset, one would need to calculate each cluster's score, and then apply the multiclass logistic regression model to the set of scores to get an assigned outcome (see main Methods). The classifier in the discovery data was tested using leave-one-out cross validation to estimate its accuracy in validation applications.

Testing of the Validation Datasets

The classifier was applied to the validation datasets, and for each validation dataset, demographic and phenotypic data for each assigned cluster were calculated. Since these datasets were tested separately, the data are presented both as means of output from each validation dataset and as a pooled output.

Next, it was determined whether the cluster assignments in the validation clusters were exhibiting the same biology as their matching clusters in the discovery data. First, each gene was scaled within its local dataset, and then took the mean of each gene within each assigned cluster within each dataset. This left a vector of mean differences for each gene within each cluster. These mean difference vectors were correlated across the discovery clusters and all validation clusters, and the results were plotted as a heatmap.

A pathways-based approach was also taken to confirm the consistency of the biology between discovery and validation clusters. Within each validation cohort, the same SAM method as above was used to assign overrepresented GO pathways to each validation cluster. Every GO pathway that was found to be significant in discovery clusters in every validation cluster was then tested, and the resulting significance levels were plotted as a heatmap, with row (GO) order determined by significance level in the discovery clusters.

E-Value Sensitivity Analysis

In order to address the possibility of unmeasured confounding in sample assignment, a sensitivity analysis based on the 'E-value' was performed (7). In this method, a given risk ratio (RR) is used to determine an 'E-value', which is the effect size that an unmeasured confounder would have to have on both the explanatory variable and the outcome variable in order to explain away the observed RR. In order to put the E-value range into context, the RRs of the already measured potentially confounding variables (here age, shock, and severity) for both the explanatory variable (cluster assignment) and the outcome variable (mortality) were tested. The resulting RRs are then compared to the calculated E-values to determine how much greater of an effect size a potential confounder would have to have in order to explain away the observed effect. In this application, it helps test the relationship between cluster assignment and mortality.

Cluster Classifier

The different datasets encompassed a broad range of microarray types, so a two-stage method of classification was built wherein a generative model (regression) is run on the outputs from parameter-free algorithms (differential gene expression), thereby overcoming technical differences between microarrays. Thus, there are two stages to the classifier: the first produces three cluster-specific scores by looking at differential gene expression. Each of three cluster-specific scores is calculated by computing the geometric mean of the 'up' genes for the given cluster, and subtracting the geometric mean of the 'down' genes. Thus, for example, the 'Inflammopathic' score is calculated as: $(ARG1*LCN2*LTF*OLFM4)^{(1/4)}-(HLADMB)$. In the second stage, a multiclass regression algorithm takes each of these three scores for each sample and produces a final prediction. This two-stage process was necessary to utilize the full breadth of data across a wide range of microarray types.

Clinical Parameters

One key clinical variable is clinical severity, as measured by a standardized score. Since each of the different datasets used different clinical severity scores (e.g. APACHE II, SOFA, SAPS, PRISM), these scores could not be pooled across datasets. Instead, for each dataset, the mean clinical severity score was calculated, and then labelled patients as either 'high clinical severity' (greater than the mean) or 'low clinical severity' (less than the mean). The percent of 'high clinical severity' patients within each cluster within each dataset was then calculated as a way of testing for clinical severity across the different datasets.

Immunosuppression status was available for two datasets (GSE63042 and GSE66099). In each case the category was binary (either immunosuppressed or not) as retrospectively recorded by the enrolling team. For GSE66099 the exact criteria is not present; for GSE63042, the composite category included absolute neutropenia, AIDS, chronic immunosuppressants or corticosteroids, chemotherapy, or 'other immunosuppressants'. The categories are thus believed to be heterogeneous.

General Methods

All analyses were conducted in the R statistical computing language, version 3.1.1. Categorical data were tested with Chi-square or Fisher Exact, and continuous data were tested with ANOVA. Significance was set at $P<0.05$ unless otherwise specified.

Supplemental Results

Discovery Cluster Assignment

At 500 genes there was an 84% agreement between the K-means and PAM algorithms in assigning samples to the 3 clusters. The 16% of samples (N=112) with disagreeing assignments were removed as 'unclustered', while the remaining samples were assigned to discovery clusters. There were varying distributions of clusters across datasets (Table 12), which was expected given the varying enrollment criteria of each dataset.

TABLE 12

Clustering in the discovery data broken out by individual dataset (A) and microarray type (B).

| | Inflammo-pathic | Adaptive | Coagulo-pathic | Unclustered |
|---|---|---|---|---|
| A: Datasets | | | | |
| EMEXP3567 | 9 | 2 | 0 | 1 |
| EMTAB1548 | 27 | 5 | 33 | 17 |
| GSE11755 | 5 | 0 | 1 | 0 |
| GSE13015 gpl6106 | 8 | 24 | 5 | 11 |
| GSE13015 gpl6947 | 2 | 8 | 1 | 4 |
| GSE20346 | 2 | 3 | 1 | 0 |
| GSE28750 | 3 | 2 | 4 | 1 |
| GSE33341 | 2 | 44 | 0 | 5 |
| GSE40012 | 2 | 13 | 2 | 4 |
| GSE40586 | 0 | 19 | 1 | 1 |
| GSE57065 | 12 | 7 | 21 | 16 |
| GSE65682 | 28 | 19 | 42 | 12 |
| GSE66099 | 76 | 58 | 31 | 23 |
| GSE69528 | 14 | 43 | 9 | 17 |
| Total | 190 | 247 | 151 | 112 |
| B: Microarray Type | | | | |
| GPL96 | 9 | 2 | 0 | 1 |
| GPL570 | 96 | 67 | 57 | 40 |
| GPL571 | 2 | 44 | 0 | 5 |
| GPL6106 | 8 | 24 | 5 | 11 |
| GPL6244 | 0 | 19 | 1 | 1 |
| GPL6947 | 6 | 24 | 4 | 8 |
| GPL10332 | 27 | 5 | 33 | 17 |
| GPL10558 | 14 | 43 | 9 | 17 |
| GPL13667 | 28 | 19 | 42 | 12 |
| Total | 190 | 247 | 151 | 112 |

In order to evaluate if the 500-gene subset was capturing most of the variance across all measured genes in the discovery data, principal components analysis (PCA) was performed. Both PCAs showed clear separation among the three clusters, with the 'unclustered' samples distributed among the three clusters (FIG. 7). A heatmap of the 500 genes used in clustering also showed clear differences between the clusters, as expected (FIG. 8).

Clinical Coagulopathy in the Coagulopathic Cluster

To investigate whether the Coagulopathic cluster had functional evidence of coagulopathy, standard measures of coagulopathy were studied to determine if they were differentially distributed across the three clusters. In the only cohort for which these data were accessible (pediatric ICU, GSE66099), disseminated intravascular coagulation (DIC) was significantly associated with the Coagulopathic cluster (P<0.05, Table 9). In another dataset (adults, CAPSOD, GSE63042), the intersection of thrombocytopenia (platelets <100,000) and prolonged INR (>1.3) was also significantly associated with the Coagulopathic cluster, though neither parameter on its own was significantly associated with cluster type (Table 10). These findings show that the Coagulopathic cluster may be associated with advanced forms of coagulopathy such as DIC, but not thrombocytopenia alone.

Comparison to Previously Established Sepsis Endotypes

Two groups have previously performed clustering using sepsis transcriptomic profiles. Wong et al. (discovery dataset GSE66099) derived three endotypes of pediatric sepsis, and have since validated two: Endotype A (higher mortality, with adaptive immune suppression and decreased glucocorticoid receptor signaling) and Endotype B (lower mortality) (9-11). Davenport et al. (validation dataset EMTAB-4421.51) derived two clusters of adult sepsis: sepsis response signature (SRS) 1 (higher mortality, with endotoxin signaling, T-cell repression, and NF-kB activation) and SRS 2 (lower mortality, with T-cell activation and interferon signaling) (12, 13). For each subject in these two cohorts, the present cluster assignments were compared to the previously published assignments (Table 10). Most samples (60 of 69) in the Inflammopathic cluster were Wong et al. Endotype B. However, the converse was not true: an additional 22 Endotype B samples were in the Adaptive cluster and 13 were in the Coagulopathic cluster. Consistent with these findings, Goodman and Kruskal's lambda showed unidirectional significance with the present clusters' ability to explain the Wong clusters, but not visa-versa. The correlations were stronger in the Davenport et al. clusters where the Inflammopathic and Adaptive clusters largely represented SRS 1 and 2, respectively. The lambda for the present clusters and the Davenport clusters was bidirectionally significant. These results suggest that Endotype B and SRS 1 may also represent the Inflammopathic cluster, while SRS 2 may represent the Adaptive cluster.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

REFERENCES

1. Singer M, Deutschman C S, Seymour C W, et al. The Third International Consensus Definitions for Sepsis and Septic Shock (Sepsis-3). JAMA 2016; 315(8):801-810.
2. Liu V, Escobar G J, Greene J D, et al. Hospital Deaths in Patients With Sepsis From 2 Independent Cohorts. JAMA 2014.
3. Opal S M, Dellinger R P, Vincent J L, et al. The next generation of sepsis clinical trial designs: what is next after the demise of recombinant human activated protein C?*. Crit Care Med 2014; 42(7):1714-1721.
4. van't Veer L J, Dai H, van de Vijver M J, et al. Gene expression profiling predicts clinical outcome of breast cancer. Nature 2002; 415(6871):530-536.
5. Golub T R, Slonim D K, Tamayo P, et al. Molecular classification of cancer: class discovery and class prediction by gene expression monitoring. Science 1999; 286 (5439):531-537.
6. Prescott H C, Calfee C S, Thompson B T, et al. Toward Smarter Lumping and Smarter Splitting: Rethinking Strategies for Sepsis and Acute Respiratory Distress Syndrome Clinical Trial Design. Am J Respir Crit Care Med 2016; 194(2):147-155.
7. Haldar P, Pavord I D, Shaw D E, et al. Cluster analysis and clinical asthma phenotypes. Am J Respir Crit Care Med 2008; 178(3):218-224.
8. Famous K R, Delucchi K, Ware L B, et al. Acute Respiratory Distress Syndrome Subphenotypes Respond Differently to Randomized Fluid Management Strategy. Am J Respir Crit Care Med 2017; 195(3):331-338.
9. Wong H R, Cvijanovich N, Lin R, et al. Identification of pediatric septic shock subclasses based on genome-wide expression profiling. BMC Med 2009; 7:34.
10. Wong H R, Cvijanovich N Z, Allen G L, et al. Validation of a gene expression-based subclassification strategy for pediatric septic shock. Crit Care Med 2011; 39(11):2511-2517.
11. Wong H R, Cvijanovich N Z, Anas N, et al. Developing a clinically feasible personalized medicine approach to pediatric septic shock. Am J Respir Crit Care Med 2015; 191(3):309-315.
12. Davenport E E, Burnham K L, Radhakrishnan J, et al. Genomic landscape of the individual host response and outcomes in sepsis: a prospective cohort study. Lancet Respir Med 2016.
13. Burnham K L, Davenport E E, Radhakrishnan J, et al. Shared and Distinct Aspects of the Sepsis Transcriptomic Response to Fecal Peritonitis and Pneumonia. Am J Respir Crit Care Med 2016.
14. Sweeney T E, Chen A C, Gevaert O. Combined Mapping of Multiple clUsteriNg ALgorithms (COMMUNAL): A Robust Method for Selection of Cluster Number, K. Sci Rep 2015; 5:16971.
15. Sweeney T E, Wong H R, Khatri P. Robust classification of bacterial and viral infections via integrated host gene expression diagnostics. Sci Transl Med 2016; 8(346): 346ra391.

16. Planey C R, Gevaert O. CoINcIDE: A framework for discovery of patient subtypes across multiple datasets. Genome Med 2016; 8(1):27.

17. Sweeney T E, Khatri P. Benchmarking Sepsis Gene Expression Diagnostics Using Public Data. Crit Care Med 2016.

18. Sweeney T E, Perumal T M, Henao R, et al. Mortality prediction in sepsis via gene expression analysis: a community approach. Nature Communications, Accepted, 2018.

19. Andres-Terre M, McGuire H M, Pouliot Y, et al. Integrated, Multi-cohort Analysis Identifies Conserved Transcriptional Signatures across Multiple Respiratory Viruses. Immunity 2015; 43(6):1199-1211.

20. Sweeney T E, Shidham A, Wong H R, et al. A comprehensive time-course-based multicohort analysis of sepsis and sterile inflammation reveals a robust diagnostic gene set. Sci Transl Med 2015; 7(287):287ra271.

21. Seok J, Warren H S, Cuenca A G, et al. Genomic responses in mouse models poorly mimic human inflammatory diseases. Proc Natl Acad Sci USA 2013; 110(9): 3507-3512.

22. Chen J, Bardes E E, Aronow B J, et al. ToppGene Suite for gene list enrichment analysis and candidate gene prioritization. Nucleic Acids Res 2009; 37 (Web Server issue): W305-311.

23. Tusher V G, Tibshirani R, Chu G. Significance analysis of microarrays applied to the ionizing radiation response. Proc Natl Acad Sci USA 2001; 98(9):5116-5121.

24. Irwin A D, Marriage F, Mankhambo L A, et al. Novel biomarker combination improves the diagnosis of serious bacterial infections in Malawian children. BMC Med Genomics 2012; 5:13.

25. Almansa R, Heredia-Rodríguez M, Gomez-Sanchez E, et al. Transcriptomic correlates of organ failure extent in sepsis. J Infect 2015; 70(5):445-456.

26. Emonts M. Polymorphisms in Immune Response Genes in Infectious Diseases and Autoimmune Diseases [Polymorphisms in Immune Response Genes in Infectious Diseases and Autoimmune Diseases; Ph.D. thesis]: Erasmus University Rotterdam; 2008.

27. Pankla R, Buddhisa S, Berry M, et al. Genomic transcriptional profiling identifies a candidate blood biomarker signature for the diagnosis of septicemic melioidosis. Genome Biol 2009; 10(11):R127.

28. Parnell G P, McLean A S, Booth D R, et al. A distinct influenza infection signature in the blood transcriptome of patients with severe community-acquired pneumonia. Crit Care 2012; 16(4):R157.

29. Sutherland A, Thomas M, Brandon R A, et al. Development and validation of a novel molecular biomarker diagnostic test for the early detection of sepsis. Crit Care 2011; 15(3):R149.

30. Ahn S H, Tsalik E L, Cyr D D, et al. Gene expression-based classifiers identify *Staphylococcus aureus* infection in mice and humans. PLoS One 2013; 8(1):e48979.

31. Parnell G P, Tang B M, Nalos M, et al. Identifying key regulatory genes in the whole blood of septic patients to monitor underlying immune dysfunctions. Shock 2013; 40(3):166-174.

32. Lill M, Koks S, Soomets U, et al. Peripheral blood RNA gene expression profiling in patients with bacterial meningitis. Front Neurosci 2013; 7:33.

33. Cazalis M A, Lepape A, Venet F, et al. Early and dynamic changes in gene expression in septic shock patients: a genome-wide approach. Intensive Care Med Exp 2014; 2(1):20.

34. Scicluna B P, Klein Klouwenberg P M, van Vught L A, et al. A molecular biomarker to diagnose community-acquired pneumonia on intensive care unit admission. Am J Respir Crit Care Med 2015; 192(7):826-835.

35. Wong H R, Shanley T P, Sakthivel B, et al. Genome-level expression profiles in pediatric septic shock indicate a role for altered zinc homeostasis in poor outcome. Physiol Genomics 2007; 30(2):146-155.

36. Wong H R, Cvijanovich N, Allen G L, et al. Genomic expression profiling across the pediatric systemic inflammatory response syndrome, sepsis, and septic shock spectrum. Crit Care Med 2009; 37(5):1558-1566.

37. Kwan A, Hubank M, Rashid A, et al. Transcriptional instability during evolving sepsis may limit biomarker based risk stratification. PLoS One 2013; 8(3):e60501.

38. Howrylak J A, Dolinay T, Lucht L, et al. Discovery of the gene signature for acute lung injury in patients with sepsis. Physiol Genomics 2009; 37(2):133-139.

39. Dolinay T, Kim Y S, Howrylak J, et al. Inflammasome-regulated cytokines are critical mediators of acute lung injury. Am J Respir Crit Care Med 2012; 185(11):1225-1234.

40. Tsalik E L, Henao R, Nichols M, et al. Host gene expression classifiers diagnose acute respiratory illness etiology. Sci Transl Med 2016; 8(322):322ra311.

41. Kangelaris K N, Prakash A, Liu K D, et al. Increased expression of neutrophil-related genes in patients with early sepsis-induced ARDS. Am J Physiol Lung Cell Mol Physiol 2015; 308(11):L1102-1113.

42. McHugh L, Seldon T A, Brandon R A, et al. A Molecular Host Response Assay to Discriminate Between Sepsis and Infection-Negative Systemic Inflammation in Critically Ill Patients: Discovery and Validation in Independent Cohorts. PLoS Med 2015; 12(12):e1001916.

43. Khoo S K, Petillo D, Parida M, et al. Host response transcriptional profiling reveals extracellular components and ABC (ATP-binding cassette) transporters gene enrichment in typhoid fever-infected Nigerian children. BMC Infect Dis 2011; 11:241.

44. Langley R J, Tsalik E L, van Velkinburgh J C, et al. An integrated clinico-metabolomic model improves prediction of death in sepsis. Sci Transl Med 2013; 5(195): 195ra195.

45. Cohen J, Vincent J L, Adhikari N K, et al. Sepsis: a roadmap for future research. Lancet Infect Dis 2015; 15(5):581-614.

46. Bernard G R, Vincent J L, Laterre P F, et al. Efficacy and safety of recombinant human activated protein C for severe sepsis. N Engl J Med 2001; 344(10):699-709.

47. Allingstrup M, Wetterslev J, Ravn F B, et al. Antithrombin III for critically ill patients: a systematic review with meta-analysis and trial sequential analysis. Intensive Care Med 2016; 42(4):505-520.

48. Shakoory B, Carcillo J A, Chatham W W, et al. Interleukin-1 Receptor Blockade Is Associated With Reduced Mortality in Sepsis Patients With Features of Macrophage Activation Syndrome: Reanalysis of a Prior Phase III Trial. Crit Care Med 2016; 44(2):275-281.

49. Shindo Y, McDonough J S, Chang K C, et al. Anti-PD-L1 peptide improves survival in sepsis. J Surg Res 2017; 208:33-39.

50. Angus D C, van der Poll T. Severe sepsis and septic shock. N Engl J Med 2013; 369(9):840-851.

51. Oved K, Cohen A, Boico O, et al. A novel host-proteome signature for distinguishing between acute bacterial and viral infections. PLoS One 2015; 10(3):e0120012.

REFERENCES FOR SUPPLEMENTAL
METHODS AND SUPPLEMENTAL RESULTS

1. Tibshirani R, Walther G, Hastie T. Estimating the number of clusters in a data set via the gap statistic. *Journal of the Royal Statistical Society Series B-Statistical Methodology* 2001; 63: 411-423.
2. Sweeney T E, Chen A C, Gevaert O. Combined Mapping of Multiple clUsteriNg ALgorithms (COMMUNAL): A Robust Method for Selection of Cluster Number, K. *Sci Rep* 2015; 5: 16971.
3. Planey C R, Gevaert O. CoINcIDE: A framework for discovery of patient subtypes across multiple datasets. *Genome Med* 2016; 8: 27.
4. Tusher V G, Tibshirani R, Chu G. Significance analysis of microarrays applied to the ionizing radiation response. *Proc Natl Acad Sci USA* 2001; 98: 5116-5121.
5. Chen J, Bardes E E, Aronow B J, Jegga A G. ToppGene Suite for gene list enrichment analysis and candidate gene prioritization. *Nucleic Acids Res* 2009; 37: W305-311.
6. Sweeney T E, Shidham A, Wong H R, Khatri P. A comprehensive time-course-based multicohort analysis of sepsis and sterile inflammation reveals a robust diagnostic gene set. *Sci Transl Med* 2015; 7: 287ra271.
7. VanderWeele T J, Ding P. Sensitivity Analysis in Observational Research: Introducing the E-Value. *Ann Intern Med* 2017.

That which is claimed is:

1. A method for treating a human subject having sepsis, comprising:
   a) receiving a report indicating that the subject has an Inflammopathic phenotype, wherein the report is based on the expression levels of RNA transcripts encoded by at least ARG1 LCN2, LTF, OLFM4 and HLA-DMB in a blood sample from the subject, wherein (i) increased ARG1, LCN2, LTF, and OLFM4 and (ii) decreased HLA-DMB relative to control subjects that have non-Inflammopathic sepsis indicates that the subject has an Inflammopathic phenotype;
   (b) identifying the subject as having an Inflammopathic phenotype based on the report; and
   (c) treating the subject having an Inflammopathic phenotype with a corticosteroid.

2. The method of claim 1, wherein the expression levels are measured by sequencing.

3. The method of claim 1, wherein the expression levels are measured by RT-PCR.

4. The method of claim 1, wherein the expression levels are measured by labeling the RNA, or cDNA made from the same; and hybridizing the labeled RNA or cDNA to a support.

5. The method of claim 1, wherein expression levels are measured using RNA isolated from whole blood, white blood cells, neutrophils or buffy coat.

6. The method of claim 1, further comprising treating the subject with one or more innate or adaptive immunity modulators selected from: abatacept, Abetimus, Abrilumab, adalimumab, Afelimomab, Aflibercept, Alefacept, anakinra, Andecaliximab, Anifrolumab, Anrukinzumab, Anti-lymphocyte globulin, Anti-thymocyte globulin, antifolate, Apolizumab, Apremilast, Aselizumab, Atezolizumab, Atorolimumab, Avelumab, azathioprine, Basiliximab, Belatacept, Belimumab, Benralizumab, Bertilimumab, Besilesomab, Bleselumab, Blisibimod, Brazikumab, Briakinumab, Brodalumab, Canakinumab, Carlumab, Cedelizumab, Certolizumab pegol, chloroquine, Clazakizumab, Clenoliximab, cyclosporine, Daclizumab, Dupilumab, Durvalumab, Eculizumab, Efalizumab, Eldelumab, Elsilimomab, Emapalumab, Enokizumab, Epratuzumab, Erlizumab, etanercept, Etrolizumab, Everolimus, Fanolesomab, Faralimomab, Fezakinumab, Fletikumab, Fontolizumab, Fresolimumab, Galiximab, Gavilimomab, Gevokizumab, Gilvetmab, golimumab, Gomiliximab, Guselkumab, Gusperimus, hydroxychloroquine, Ibalizumab, Immunoglobulin E, Inebilizumab, infliximab, Inolimomab, Integrin, Interferon, Ipilimumab, Itolizumab, Ixekizumab, Keliximab, Lampalizumab, Lanadelumab, Lebrikizumab, leflunomide, Lemalesomab, Lenalidomide, Lenzilumab, Lerdelimumab, Letolizumab, Ligelizumab, Lirilumab, Lulizumab pegol, Lumiliximab, Maslimomab, Mavrilimumab, Mepolizumab, Metelimumab, methotrexate, minocycline, Mogamulizumab, Morolimumab, Muromonab-CD3, Mycophenolic acid, Namilumab, Natalizumab, Nerelimomab, Nivolumab, Obinutuzumab, Ocrelizumab, Odulimomab, Oleclumab, Olokizumab, Omalizumab, Otelixizumab, Oxelumab, Ozoralizumab, Pamrevlumab, Pascolizumab, Pateclizumab, PDE4 inhibitor, Pegsunercept, Pembrolizumab, Perakizumab, Pexelizumab, Pidilizumab, Pimecrolimus, Placulumab, Plozalizumab, Pomalidomide, Priliximab, purine synthesis inhibitors, pyrimidine synthesis inhibitors, Quilizumab, Reslizumab, Ridaforolimus, Rilonacept, rituximab, Rontalizumab, Rovelizumab, Ruplizumab, Samalizumab, Sarilumab, Secukinumab, Sifalimumab, Siplizumab, Sirolimus, Sirukumab, Sulesomab, sulfasalazine, Tabalumab, Tacrolimus, Talizumab, Telimomab aritox, Temsirolimus, Teneliximab, Teplizumab, Teriflunomide, Tezepelumab, Tildrakizumab, tocilizumab, tofacitinib, Toralizumab, Tralokinumab, Tregalizumab, Tremelimumab, Ulocuplumab, Umirolimus, Urelumab, Ustekinumab, Vapaliximab, Varlilumab, Vatelizumab, Vedolizumab, Vepalimomab, Visilizumab, Vobarilizumab, Zanolimumab, Zolimomab aritox, Zotarolimus, or recombinant human cytokines.

7. The method of claim 1, further comprising treating the subject with a blockade or signaling modification of PD1, PDL1, CTLA4, TIM-3, BTLA, TREM-1, LAG3, VISTA, or any of the human clusters of differentiation, including CD1, CD1a, CD1b, CD1c, CD1d, CD1e, CD2, CD3, CD3d, CD3e, CD3g, CD4, CD5, CD6, CD7, CD8, CD8a, CD8b, CD9, CD10, CD11a, CD11b, CD11c, CD11d, CD13, CD14, CD15, CD16, CD16a, CD16b, CD17, CD18, CD19, CD20, CD21, CD22, CD23, CD24, CD25, CD26, CD27, CD28, CD29, CD30, CD31, CD32A, CD32B, CD33, CD34, CD35, CD36, CD37, CD38, CD39, CD40, CD41, CD42, CD42a, CD42b, CD42c, CD42d, CD43, CD44, CD45, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64a, CD65, CD65s, CD66a, CD66b, CD66c, CD66d, CD66e, CD66f, CD68, CD69, CD70, CD71, CD72, CD73, CD74, CD75, CD75s, CD77, CD79A, CD79B, CD80, CD81, CD82, CD83, CD84, CD85A, CD85B, CD85C, CD85D, CD85F, CD85G, CD85H, CD85I, CD85J, CD85K, CD85M, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD107a, CD107b, CD108, CD109, CD110, CD111, CD112, CD113, CD114, CD115, CD116, CD117, CD118, CD119, CD120, CD120a, CD120b, CD121a, CD121b, CD122, CD123, CD124, CD125, CD126, CD127, CD129, CD130, CD131, CD132, CD133, CD134, CD135, CD136, CD137, CD138, CD139, CD140A, CD140B, CD141, CD142, CD143, CD144, CDw145, CD146, CD147, CD148, CD150, CD151, CD152, CD153, CD154, CD155, CD156, CD156a, CD156b, CD156c, CD157, CD158, CD158A, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD187, CD188, CD189, CD190, CD191, CD192, CD193, CD194, CD195, CD196, CD197, CDw198, CDw199, CD200, CD201, CD202b, CD203c, CD204, CD205, CD206, CD207, CD208, CD209, CD210, CDw210a, CDw210b, CD211, CD212, CD213a1, CD213a2, CD214, CD215, CD216, CD217, CD218a, CD218b, CD219, CD220, CD221, CD222, CD223, CD224, CD225, CD226, CD227, CD228, CD229, CD230, CD231, CD232, CD233, CD234, CD235a, CD235b, CD236, CD237, CD238, CD239, CD240CE, CD240D, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CDw293, CD294, CD295, CD296, CD297, CD298, CD299, CD300A, CD300C, CD301, CD302, CD303, CD304, CD305, CD306, CD307, CD307a, CD307b, CD307c, CD307d, CD307e, CD308, CD309, CD310, CD311, CD312, CD313, CD314, CD315, CD316, CD317, CD318, CD319, CD320, CD321, CD322, CD323, CD324, CD325, CD326, CD327, CD328, CD329, CD330, CD331, CD332, CD333, CD334, CD335, CD336, CD337, CD338, CD339, CD340, CD344, CD349, CD351, CD352, CD353, CD354, CD355, CD357, CD358, CD360, CD361, CD362, CD363, CD364, CD365, CD366, CD367, CD368, CD369, CD370, or CD371.

8. The method of claim 1, wherein the report indicates whether the subject is male, the age of the subject, white blood cell count, neutrophils count, band count, lymphocyte count, monocyte count, whether the subject is immunosuppressed, and/or whether there are Gram-negative bacteria present.

9. The method of claim 1, wherein the report indicates expression levels of RNA transcripts encoded by at least 3, at least 5, at least 10, at least 15, at least 20, at least 25 or all of YKT6, PDE4B, TWISTNB, BTN2A2, ZBTB33, PSMB9, CAMK4, TMEM19, SLC12A7, TP53BP1, PLEKHO1, SLC25A22, FRS2, GADD45A, CD24, S100A12, STX1A, KCNMB4, CRISP2, HTRA1, PPL, RHBDF2, ZCCHC4, YKT6, DDX6, SENP5, RAPGEF1, DTX2 and RELB in the sample.

* * * * *